(12) United States Patent
Tümer

(10) Patent No.: US 7,566,879 B2
(45) Date of Patent: Jul. 28, 2009

(54) METHOD AND APPARATUS FOR RADIATION DETECTION

(76) Inventor: Tümay O. Tümer, c/o NOVA R & D, Inc., 1525 Third St., Suite C, Riverside, CA (US) 92507

( * ) Notice: Subject to any disclaimer, the term of this patent is extended or adjusted under 35 U.S.C. 154(b) by 0 days.

(21) Appl. No.: 11/378,255

(22) Filed: Mar. 20, 2006

(65) Prior Publication Data

US 2007/0045547 A1 Mar. 1, 2007

Related U.S. Application Data

(60) Continuation of application No. 11/044,207, filed on Jan. 28, 2005, now Pat. No. 7,034,310, which is a continuation of application No. 10/420,897, filed on Apr. 23, 2003, now Pat. No. 7,060,983, which is a continuation of application No. 10/175,084, filed on Jun. 20, 2002, now abandoned, which is a continuation of application No. 09/822,177, filed on Apr. 2, 2001, now Pat. No. 6,420,711, which is a division of application No. 09/135,184, filed on Aug. 17, 1998, now Pat. No. 6,236,050, which is a continuation-in-part of application No. 08/784,176, filed on Jan. 15, 1997, now Pat. No. 5,821,541.

(60) Provisional application No. 60/011,135, filed on Feb. 2, 1996.

(51) Int. Cl.
*G01T 1/29* (2006.01)

(52) U.S. Cl. .............................. 250/370.1; 250/370.09

(58) Field of Classification Search .............. 250/370.1, 250/370.09
See application file for complete search history.

(56) References Cited

U.S. PATENT DOCUMENTS 4,262,202 A    4/1981 Cusano et al.
4,529,882 A    7/1985 Lee
4,833,327 A    5/1989 Hart
4,857,737 A    8/1989 Kamae
4,914,300 A    4/1990 Kalish
5,008,493 A    4/1991 Wagener (Continued)

OTHER PUBLICATIONS

Solomon, Christopher J. et al., "Gamma Ray Imaging With Silicon Detectors—A Compton Camera for Radionuclide Imaging in Medicine," *Nuclear Instruments and Methods in Physics Research* A273, Dec. 15, 1998, pp. 787-792.

(Continued)

*Primary Examiner*—David P Porta
*Assistant Examiner*—Jessica L Eley
(74) *Attorney, Agent, or Firm*—Fish & Associates, PC

(57) ABSTRACT

An imaging system for imaging an object has an x-ray source for emitting x-rays. A detection system has a plurality of position sensitive detector planes, and the object is located between the x-ray source and the detection system. A portion of the x-rays pass through said object and pass into said plurality of detector planes and are detected within the plurality of detector planes. A multi-channel readout system is coupled to the plurality of position sensitive detector planes. A display system is coupled to the multi-channel readout system, and the display system displays an image of said object. A portion of the x-rays passing into the plurality of detector planes undergoes at least one Compton scatter within the plurality of detection planes and is detected. A total or partial energy corresponding to each portion of the emitted x-rays is recorded by a multichannel readout system. The direction for the said detected x-ray is determined and the direction and total or partial energy corresponding to each detected x-ray is processed by a multi-channel readout system to generate said image.

49 Claims, 17 Drawing Sheets

U.S. PATENT DOCUMENTS

| | | | |
|---|---|---|---|
| 5,099,128 A * | 3/1992 | Stettner | 250/370.11 |
| 5,105,087 A * | 4/1992 | Jagielinski | 250/370.09 |
| 5,117,114 A * | 5/1992 | Street et al. | 250/370.11 |
| 5,132,542 A * | 7/1992 | Bassalleck et al. | 250/370.09 |
| 5,245,191 A * | 9/1993 | Barber et al. | 250/363.04 |
| 5,336,879 A * | 8/1994 | Sauer | 250/208.1 |
| 5,357,110 A | 10/1994 | Statham | |
| 5,374,824 A | 12/1994 | Chaney et al. | |
| 5,379,336 A * | 1/1995 | Kramer et al. | 378/98.8 |
| 5,381,013 A * | 1/1995 | Cox et al. | 250/370.09 |
| 5,381,014 A * | 1/1995 | Jeromin et al. | 250/370.09 |
| 5,390,225 A | 2/1995 | Hawman | |
| 5,464,984 A * | 11/1995 | Cox et al. | 250/370.11 |
| 5,532,122 A | 7/1996 | Drukier | |
| 5,567,944 A * | 10/1996 | Rohe et al. | 250/370.09 |
| 5,600,144 A | 2/1997 | Worstell | |
| 5,635,718 A * | 6/1997 | DePuydt et al. | 250/370.09 |
| 5,665,971 A | 9/1997 | Chen et al. | |
| 5,696,458 A | 12/1997 | Tümer et al. | |
| 5,696,806 A | 12/1997 | Grodzins et al. | |
| 5,742,056 A | 4/1998 | Valentino et al. | |
| 5,742,060 A * | 4/1998 | Ashburn | 250/370.09 |
| 5,751,000 A | 5/1998 | McCroskey et al. | |
| 5,753,917 A | 5/1998 | Engdahl | |
| 5,786,597 A * | 7/1998 | Lingren et al. | 250/370.09 |
| 5,793,045 A | 8/1998 | DiFilippo et al. | |
| 5,812,191 A * | 9/1998 | Orava et al. | 348/308 |
| 5,821,541 A | 10/1998 | Tümer | |
| 5,841,141 A | 11/1998 | Gulberg et al. | |
| 6,175,116 B1 | 1/2001 | Gagnon et al. | |
| 6,236,050 B1 | 5/2001 | Tumer | |
| 6,346,706 B1 | 2/2002 | Rogers et al. | |
| 6,396,898 B1 * | 5/2002 | Saito et al. | 378/19 |
| 6,420,711 B2 | 7/2002 | Tümer | |
| 6,442,233 B1 | 8/2002 | Grodzins et al. | |
| 6,448,560 B1 | 9/2002 | Tumer | |
| 6,484,051 B1 | 11/2002 | Daniel | |

OTHER PUBLICATIONS

Tumer, Tumay O. et al., "A High Sensitivity Electronically Collimated Gamma Camera," *IEEE Transactions on Nuclear Science*, Jun. 1997, vol. 44, No. 3, pp. 899-904.

Tumer, O.T. et al., "The TIGRE Instrument for 0.3-100 MEV Gamma-Ray Astronomy," *Transactions on Nuclear Science*, vol. 42, No. 4 (Aug. 1995) pp. 907-916.

Phillips, Gary W., "Gamma-Ray Imaging With Compton Cameras," *Nuclear Imaging and Methods in Physics Research*, May 1995, pp. 674-677.

Alpar, A. et al., "Tracking and Imaging Gamma Ray Experiment (TIGRE) for 1 to 100 Mev Gamma Ray Astronomy," *Tr. J. of Physics*, Dec. 23, 1994, vol. 18, pp. 878-885.

Tumer, O. Tumay et al., "A New Telescope for Wide-Band Gamma-Ray Astronomy: The Silicon Compton Recoil Telescope (SCRT)," *The Astrophysical Journal Supplement Series*, Jun. 1994, vol. 92, pp. 671-674.

Martin, J.B. et al., "A Ring Compton Scatter Camera for Imaging Medium Energy Gamma Rays," 0-7803-0883-2/93 IEEE pp. 58-60.

McKisson, J.E. et al., "Event-Restricted Monte Carlo Situations for Compton Telescope Image Reconstruction Studies," 0-7803-0883-2/93 IEEE, pp. 667-669.

O'Neill, T.J. et al., "Compton Recoil Electron Tracking With Silicon Strip Detectors," *IEEE Transactions on Nuclear Science*, Aug. 1992, vol. 39, No. 4, pp. 629-634.

Ait-Ouamer et al., "Calibration and Performance of the UCR Double Compton Gamma Ray Telescope." *IEEE Transactions on Nuclear Science*, Apr. 1990, vol. 37, No. 2, pp. 535-540.

Kamae, T. et al., "A New Method to Measure Energy, Direction, and Polarization of Gamma Rays," *Nuclear Instruments and Methods in Physics Research*, A260, Oct. 1987, pp. 254-257.

\* cited by examiner

METHOD AND APPARATUS FOR RADIATION DETECTION

CROSS-REFERENCES TO RELATED APPLICATIONS

This application is a continuation of U.S. application Ser. No. 11/044,207 filed Jan. 28, 2005, now U.S. Pat. No. 7,034,310, which was a continuation of U.S. application Ser. No. 10/420,897, filed Apr. 23, 2003, now U.S. Pat. No. 7,060,983, which was a continuation of U.S. application Ser. No. 10/175,084, filed Jun. 20, 2002 (now abandoned), which was a continuation of U.S. application Ser. No. 09/822,177, filed Apr. 2, 2001, now U.S. Pat. No. 6,420,711, which was a divisional of U.S. application Ser. No. 09/135,184, filed Aug. 17, 1998, now U.S. Pat. No. 6,236,050 which was a continuation-in-part of U.S. application Ser. No. 08/784,176, filed Jan. 15, 1997, now U.S. Pat. No. 5,821,541, which is a continuation of U.S. Provisional Application Ser. No. 60/011,135, filed Feb. 2, 1996. Applicant claims copendency with all of the above-mentioned applications which are incorporated herein by reference.

GOVERNMENT RIGHTS NOTICE

This invention was made with U.S. Government support under Contract Numbers DASG60-92-C-0200 and DAAA21-93-C-1014, both awarded by the Department of Defense. The U.S. Government has certain rights in the invention.

FIELD OF THE INVENTION

The present invention relates generally to detection systems, and more particularly, to a method and apparatus for imaging gamma rays, x-rays, and positrons.

BACKGROUND OF THE INVENTION

The dominant absorption process for gamma rays of about 0.05 to 30 MeV is the Compton interaction. At present the best method to detect these gamma rays is the Compton double scatter technique since single Compton scattering alone gives neither the direction nor the energy of the incident gamma ray. In contrast, the Compton double scatter technique yields both the direction and the energy of the incoming photon.

Present detectors which use the Compton double scatter technique determine the direction of the incoming photon to a ring in the sky since the direction of the recoil electron at the first scatter cannot be measured. Time-of-flight measurements are normally used to discriminate between gamma rays coming through the field-of-view and those entering through the back of the system. Typically this requires that the first scatterer (i.e., the hodoscope) is separated from the second scatterer (i.e., calorimeter) by approximately 1.5 meters.

Emission computed tomography (ECT) and associated technologies are mainly used for the detection and imaging of the radiation produced by radiotracers and radiopharmaceuticals. The primary application for ECT systems is in medical study and diagnosis due to the potential for imaging organ functions in real time. The two major ECT instruments presently used are Single Photon Emission Computed Tomography (SPECT) and Positron Emission Tomography (PET).

Positron scanners for use in locating brain tumors were first developed in the early 1960s with the first PET system completed in 1975. Pet systems have become an essential medical diagnostic tool for a variety of reasons. For one, very high efficiencies utilizing positron emitting labels can be achieved through the coincidence collimation of the annihilation radiation. Another advantage is that the common radiopharmaceuticals used with PET systems typically have very short life times, thus allowing large doses to be administered to a patient as well as the performance of repetitive studies. Recently, the utilization of photon time-of-flight information with fast scintillators has improved the SNR that can be obtained in images of the distribution of positron emitting radionuclides.

Present PET systems use bismuth germanate oxide (BGO) crystals. BGO crystals have the highest effective atomic number and stopping power of any scintillator crystal available today. This translates into a higher photopeak fraction and a lower Compton continuum than other crystals such as NaI and $BaF_2$. Gadolinium orthosilicate (GSO) crystal is an alternative which has a slower decay time but larger pulse yield than BGO. $PbCO_3$ crystals nearly equal the stopping power of BGO but the light output is about 10 times lower.

From the foregoing, it is apparent that an improved imaging system for use with gamma rays, x-rays, and positrons is desired.

SUMMARY OF THE INVENTION

The present invention provides a high sensitivity, low background detector for use in a variety of applications. The detector also has excellent angular resolution for accurate direction measurement and imaging; good energy resolution for the identification of the source material by its energy spectrum; and low power consumption. Both the direction and energy of the incident photons is measured using a Compton double scatter technique with recoil electron tracking.

The Compton double scatter technique involves two detector layers; a silicon microstrip hodoscope and a calorimeter. The incoming photon Compton scatters in the hodoscope. The second scatter layer is the calorimeter where the scattered gamma ray is totally absorbed. The recoil electron in the hodoscope is tracked through several detector planes until it stops. The x and y position signals from the first two planes of the electron track determine the direction of the recoil electron. The energy loss from all planes is summed to determine the energy of the recoil electron.

The hodoscope of the disclosed system is constructed of position sensitive, double-sided silicon microstrip detectors, preferably with a strip pitch of between 0.5 and 1 millimeter and a thickness of between 200 and 1000 micrometers. The pixel size of the microstrip detectors ranges from approximately 1 square millimeter to approximately 1 square centimeter.

The measurement of the direction of the Compton recoil electron track reduces the incident gamma ray event ring to an event arc. The recoil electron direction calculation requires only the x and y coordinates of the first two adjacent planes along the track of the recoil electron. For the measurement of the direction of motion of the recoil electron (i.e., moving forward or backward in the hodoscope) a track which penetrates 2 or more adjacent planes is required. If the energy of the recoil electron is low enough, it may be absorbed in the same detector plane and not produce a track. Thus for a 200 micrometer thick detector, recoil electron tracking is effective for electrons with an energy of greater than 0.25 MeV energy. Therefore gamma rays with energies greater than 1 MeV will produce recoil electron tracks with high probability. For low energy gamma rays which do not produce recoil electron tracks, imaging is carried out using event rings instead of arcs.

This technique increases the background, resulting in a decrease in sensitivity for low energy gamma rays. By utilizing thinner detectors the recoil electron tracking threshold can be reduced to even lower energies.

The selection of the detector for use as the second scatterer depends primarily upon the desired detection energy as well as the desired detection energy range. In one embodiment of the invention, the second scatterer uses thallium activated cesium iodide (i.e., CsI(Tl)) detectors viewed by photodiodes. In a second embodiment used to obtain higher energy resolution, a germanium array calorimeter is used. The germanium array requires refrigeration to liquid nitrogen temperatures. Alternatively, a detection system using only a hodoscope with a large number of silicon detector planes can be used for high energy resolution.

The double Compton scatter measurement determines the direction of the incident photon to a cone with a half angle equal to the scatter angle. This type of measurement requires special data analysis software. The data analysis can be carried out by cone interaction, Maximum Likelihood or Maximum Entropy techniques or using a direct data analysis and imaging technique such as Direct Linear Algebraic Deconvolution (DLAD).

In another embodiment of the invention, a Compton scatter PET system is provided. This system can be designed as a cylindrical detector with a length of approximately 30 centimeters or greater. Cylindrical geometry leads to the production of accurate 3-dimensional images. Alternately, a ring detector with a width of about 7 centimeters or less can be used to provide a multi-slice ring type system. Since the PET system according to the present invention does not utilize PMTs, it is substantially less bulky than present systems. As a result, the structural requirements placed on the gantry are less stringent.

Photon attenuation inside the patient can be corrected using the techniques already developed. For example, the boundary method has already been successfully applied to attenuation correction in PET image reconstruction. In this method, the organ boundaries are determined by transmission tomography and each region is enclosed by a boundary and assigned an average attenuation coefficient. Attenuation correction factors for all angular views can be calculated from the quantized image.

The PET embodiment of the present invention preferably uses thin film strip detectors with high stopping power such as position sensitive, double-sided CdZnTe strip detectors with an approximate strip size of at least 0.1 millimeters in both the x and y dimensions. The CdZnTe detectors have a thickness in the range of 250 micrometers to 2 millimeters. This embodiment uses several planes of detectors with minimal detection plane spacing. The incident photons undergo Compton scatter in one of the detector planes, which is the dominant process for photons above approximately 200 keV in CdZnTe. The energy of the Compton recoil electron in this detector wafer is measured. This process is repeated until the scattered photon with reduced energy either gets absorbed through the photoelectric effect in another detector plane or escapes without further interaction. If the scattered photon is fully absorbed within the detector planes, the sum of the measured energies yields the total energy of the incident photon. The straight line (i.e., cord) joining the first interaction points of an annihilation photon pair at the CdZnTe strip detector in coincidence will determine the geometry. Escaped photons will produce a tail at lower energies in the energy spectrum. Such events can be rejected because the measured total energy is smaller than the expected energy of the known incident energy of 511 keV.

A further understanding of the nature and advantages of the present invention may be realized by reference to the remaining portions of the specification and the drawings.

DESCRIPTION OF THE SPECIFIC EMBODIMENTS

Gamma Ray Detection

The most probable interaction mechanism for 0.05 to 10 MeV gamma rays in silicon is the Compton scatter process. Therefore, the detection of gamma rays in this energy range must use Compton interaction to have maximum sensitivity. The detector must also have excellent angular and energy resolution and a wide field-of-view. The best detection technique that has all of these features is the Compton double scatter method. This technique incorporates Compton scattering, photoelectric absorption, and pair production. The three gamma ray interaction mechanisms are briefly discussed below.

Although a number of possible interaction mechanisms are known for gamma rays in matter, only three major types play an important role in radiation detection: photoelectric absorption, Compton scattering, and pair production. Of these, only the first two play a major roll in emission imaging. All of these processes lead to the partial or complete transfer of the photon energy to electron energy. They result in sudden and abrupt changes in the photon history where the photon disappears entirely or is scattered through a significant angle.

Figure 1:
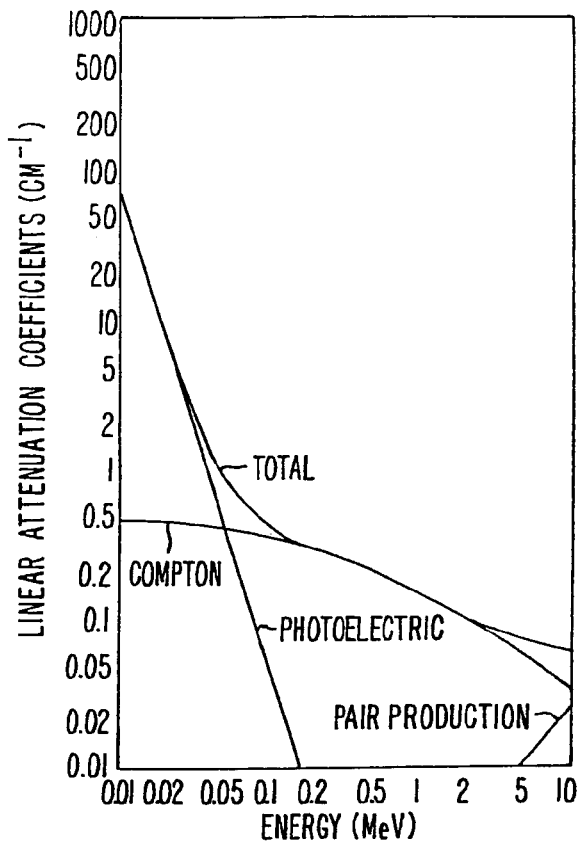
FIG. 1 is an illustration of the gamma ray linear attenuation coefficients for a silicon detector.

FIG. 1 is an illustration of the gamma ray linear attenuation coefficients for silicon microstrip detectors through these three processes. The photoelectric absorption dominates below about 50 keV for silicon. Compton scattering becomes important at 80 keV and it stays the dominant process up to about 10 MeV, where pair production takes over. Compton scattered gamma ray photons with energies less than 50 keV are readily absorbed due to the photoelectric effect.

In the photoelectric absorption process, a photon undergoes an interaction with an absorber atom in which the photon completely disappears. In its place, an energetic photoelectron is ejected by the atom from one of its bound shells. The interaction is with the atom as a whole and cannot take place with free electrons. The photoelectron appears with an energy, $E_e$, given by $$E_e = h\upsilon - E_b$$

where $h\upsilon$ is the incident photon energy and $E_b$ represents the binding energy of the photoelectron in its original shell. For gamma ray energies, $h\upsilon$, of more than a 100 keV, the photoelectron carries off most of the original photon energy. For silicon microstrip detectors, this process is only important for low energy gamma rays in the range of 0.5 to 50 keV. For CsI(Tl) crystals the photoelectric effect is dominant up to about 0.3 MeV above which Compton scattering becomes important. Photoelectric absorption falls nearly exponentially with an increase in energy. Photoelectric absorption is excellent for the determination of the scattered photon energy as the photon is completely absorbed.

Figure 2:
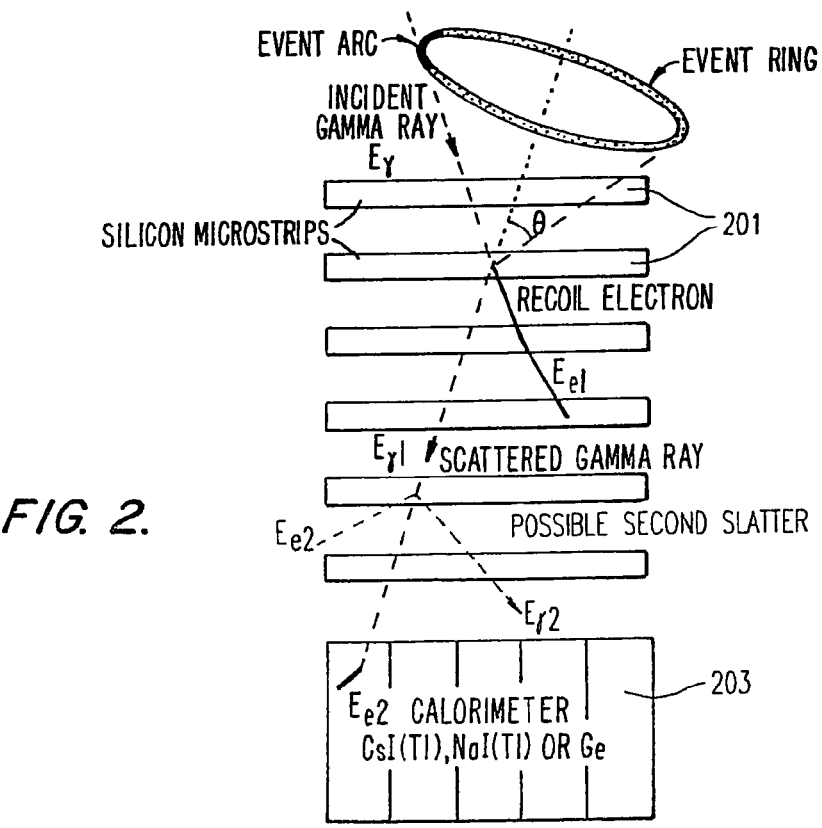
FIG. 2 is an illustration of the Compton double scatter technique for detecting gamma rays.

Compton scattering takes place between the incident gamma ray and an electron in the absorbing material. In Compton scattering, the incident gamma ray is deflected through an angle $\theta$ with respect to its original direction as illustrated in FIG. 2. The photon transfers a portion of its energy to the recoil electron that was initially at rest. Because all angles of scattering are possible, the energy transferred to the electron can vary from zero to a large fraction of the gamma ray energy. This has been a problem in the detection of gamma rays at energies dominated by the Compton scatter process, since the detected recoil electron alone does not give sufficient information to uniquely determine the energy and direction of the incident photon. This has been solved by the Compton double scatter technique described below and illustrated in FIG. 2.

The total incident gamma ray energy, $E_\gamma$, and Compton scatter angle, $\theta$, for the double scatter process are given by:

$$E_\gamma = E_{e1} + E_{\gamma 1}$$

and $$\cos\theta = 1 - mc^2(1/E_{\gamma 1} - 1/E_\gamma)$$

The incident gamma ray first scatters by the Compton process in one of the silicon strip detectors 201, losing recoil energy $E_{e1}$. The scattered photon continues on until it interacts with another silicon strip detector or is absorbed by a calorimeter 203. If the second interaction is photoelectric absorption, the full energy of the scatter photon is measured and the energy of the incident photon and the scatter angle are determined. This is the dominant process for the calorimeter as it is made of high Z material and photoelectric absorption increases exponentially with a decrease in the scattered photon energy. Another possibility is that the second interaction can be another Compton scatter where the photon escapes with a small amount of the energy. If the energy of the escaping photon is sufficiently low, the energy determination is not significantly effected. If there are enough silicon planes, the escaped photon makes further interactions in subsequent planes and gets fully absorbed by the photoelectric effect. All of the energy measured after the second scatter is just added to the energy of the second scatter, $E_{e2}$, to correct for the missing energy. If not enough silicon planes are used, for example due to cost considerations, a calorimeter can be placed such that it surrounds the sides and the bottom of the silicon strip detector hodoscope. The surrounding calorimeter is used as a second scatterer to measure the energy and direction of the scattered photon or to catch the escaping photons and correct $E_{e2}$ for accurate incident photon scatter angle determination. Since the calorimeter is a high Z and high density detector or scintillator, there is a high probability that the escaped low energy photon will be fully absorbed. The events that do not add up to the full energy of the incident photon are rejected to reduce scattered photon background, The incident gamma ray direction lies on a cone segment in the field-of-view with a half-angle $\theta$. The cone axis is determined by the interaction positions in the first and the second scatters. This is because the direction of the scattered electron in the top scintillator is not measured. The Compton scattered electrons with energies in the range of 81 to 364 keV are fully stopped within 0.03 and 0.3 millimeters of the silicon strip detectors, respectively.

For a gamma ray with an energy larger than or equal to twice the rest mass of an electron, pair production becomes energetically possible. Since the probability of an occurrence remains very low until the gamma ray approaches an energy of several MeV, pair production is confined to high energy gamma rays. In the interaction which takes place in the coulomb field of a nucleus, a gamma ray photon disappears and is replaced by an electron-positron pair. All excess energy carried by the photon above 1.022 MeV, the energy required to create the pair, goes into kinetic energy shared by the electron and the positron. The positron annihilates with an electron after slowing down in he absorbing medium and produces two annihilation photons each with an energy of 0.511 MeV in the para state or 3 photons with different energies adding to 1.022 MeV in the ortho state. The para state decay to 2 photons dominates ortho state decay.

For silicon microstrip detectors, pair production becomes significant for gamma rays above 10 MeV and dominates Compton scattering above 15 MeV. Pair events are easily distinguishable as they produce two tracks starting from a common vertex. Multiple scattering in the silicon planes quickly separate the two tracks which resemble an inverted V. Both the electron and the positron loose their energy in the silicon planes and stop. The positron quickly annihilates with an electron as it stops and creates back-to-back 0.511 MeV gamma rays. One or more of the annihilation gamma rays will likely be detected in the calorimeter in coincidence with the electron-positron pair observed in the silicon microstrip hodoscope.

Silicon Microstrip Detectors

In the preferred embodiment of the invention, silicon microstrip detectors are used as the first scatterer (i.e., hodoscope). Silicon microstrip detectors have large active areas, excellent energy and position resolution, and fast readout. Three inch (76.2 mm) diameter wafers, typically 200 to 1500 micrometers thick, with parallel readout strips of greater than 25 micrometers pitch on one side have been available for several years. Pitch size can have any value from 25 micrometers to several centimeters.

On the average, 1 electron-hole pair is produced per 3.6 eV of deposited energy. The energy deposited by an 80 keV recoil electron fully stopped in silicon is about 22,000 electrons (and holes) which can be collected in less than 10 nanoseconds. This leads to pulse rise times of less than 10 nanoseconds. Spatial resolutions of less than 10 micrometers in one dimension are obtainable by exploiting charge division between adjacent strips. Superimposed on the signal is Gaussian-distributed noise related to the detector strip and preamplifier input capacitances. This noise or equivalent noise charge (e.g., ENC) is typically about 1,000 electrons at room temperature for detector capacitances of about 20 pF. Thus large signal-to-noise ratios, on the order of 22, are obtainable for 80 keV electrons.

To date, silicon detectors have been primarily used in high energy physics experiments to detect minimum ionizing high energy charged particles. The Compton converter in the present invention is different in that the recoil electron loses varying fractions of its energy at each detector wafer that it traverses until it completely stops. The energy and angular resolutions improve as the number of electron-hole pairs created in the silicon increase. For a 300 keV recoil electron stopping in silicon, about 83,000 electrons (i.e., 278 e/keV) are produced with an inherent energy resolution of 0.8 percent (i.e., $FWHM/E_0=2.35/\sqrt{N}$ where N is the number of electron-hole pairs). For 141 keV electrons stopping inside the silicon wafer, the theoretical energy resolution is calculated to be about 1.2 percent with a stopping distance for the recoil electron of about 0.1 millimeters. The theoretical resolution can be approached if the input capacitance and the preamplifier noise can be kept low. The input capacitance can be decreased substantially by mounting the chips next to the strips or building them on the same silicon. In the present invention preferably a low noise, 64 channel front end mixed signal application specific integrated circuit (ASIC) readout chips is used.

The individual detector thicknesses can be increased in order to decrease the number of required planes. By increasing the thickness of the individual detectors, the energy resolution is improved while the accuracy of the recoil electron direction determination is decreased. The optimum thickness is also driven by the desired energy range of the detector.

Figure 3:
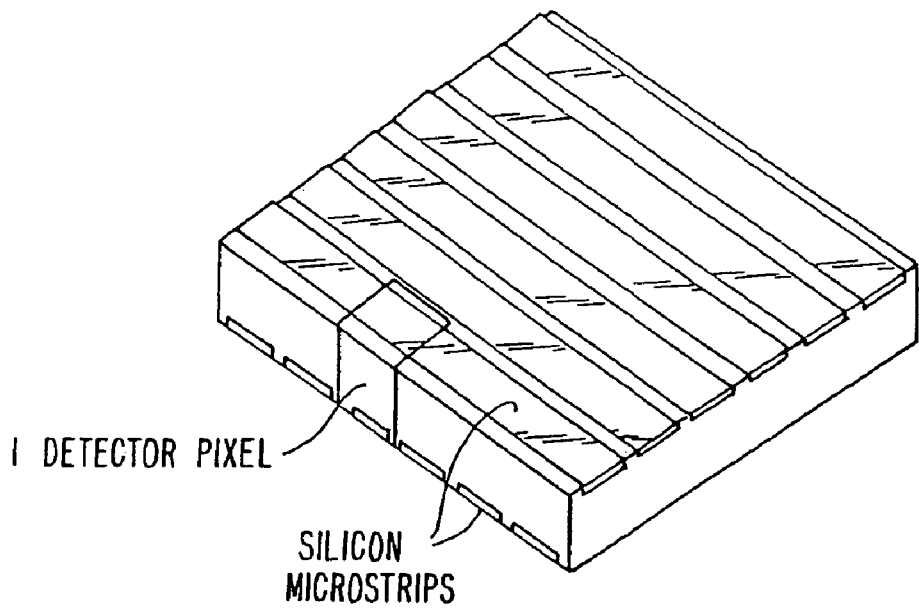
FIG. 3 is an illustration of a typical double-sided silicon microstrip or strip detector.
Figure 4:
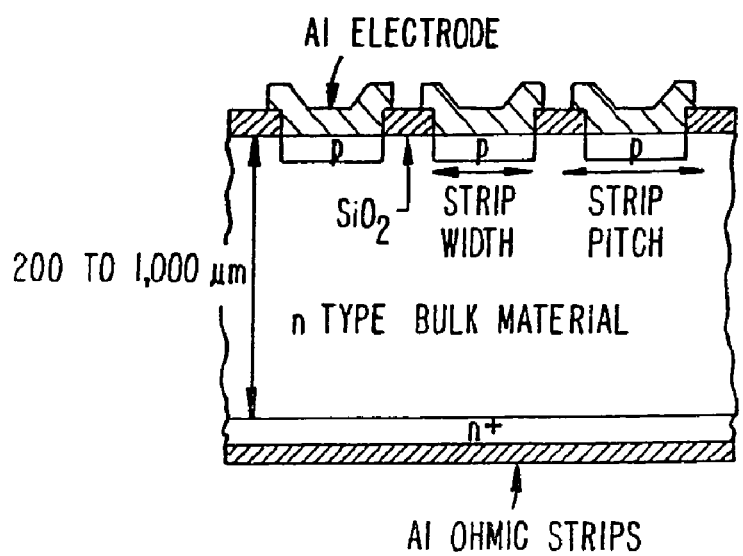
FIG. 4 is an illustration of the cross-section of the detector shown in FIG. 3.

Double-sided readout silicon microstrip detectors with orthogonal strips on opposite sides have been developed. FIGS. 3 and 4 show the basic features of a double-sided silicon microstrip or strip detector. The distinct advantage with this configuration is that both x and y coordinates of a traversing particle are determined in a single detector plane. For single-sided detectors, the junction side of a standard p+n diode is segmented into many strips. For double-sided detectors, the ohmic side of the n-type silicon wafer is also segmented with orthogonal strips to provide simultaneous readout of the particle impact point. Position resolutions well below a square millimeter on both sides can be achieved. The preferred detector in the present invention uses 200 to 1500 micrometer thick, and more preferably 200 to 300 micrometer thick, double-sided, silicon microstrip detectors with about a millimeter spaced strips orthogonal on the top and bottom surfaces. Such detectors are now commercially available and fit well with the present design. The x and y positions of the first two interaction points on the recoil electron track determine the electron direction, A combination of all interactions is used to determine the energy of the recoil electron as well as the scatter angle.

In one embodiment of the invention, the detector is 6.4 centimeters by 6.4 centimeters, the detector being fabricated from a 4 inch wafer. In another embodiment, 10 centimeter by 10 centimeter detectors are used. Bridged detectors with overall lengths exceeding 25 centimeters can also be used with the present invention. Bridging allows one preamplifier to be connected to a series of strips on adjacent detectors with significant savings in electronics.

A simple Monte Carlo calculation using Monte Carlo Neutron Photon (MCNP) software from Los Alamos National Laboratory was performed. The MCNP software gives the probability for a 141 keV photon to Compton scatter in varying total silicon thicknesses. For example, about 50 percent of the 141 keV photons will Compton scatter in a silicon detector 2 centimeters thick. If 2 millimeter thick silicon strip detectors are used, then 10 planes will be required. For lower energy photons, a lower total thickness is required.

The FWHM angular resolution of the scatter angle in a Compton double scatter detector depends on the geometry of the detector as well as its energy resolution. The FWHM uncertainty in the cone half-angle, $\Delta\theta$, due to a detector of finite energy resolution at first and second scattering planes, can be calculated using the Compton scatter formula:

$$\Delta\theta = \frac{mc^2}{E_\gamma^2 \sin\theta}\left\{\Delta E_{e1}^2 + \left[\frac{E_\gamma^2}{E_{\gamma 1}^2} - 1\right]^2 \Delta E_{e2}^2\right\}^{1/2}$$

where $mc^2$ is the electron rest energy (511 keV), $\theta$ is the Compton scatter angle, and $E_\gamma$ and $E_{\gamma 1}$ are the incident and scattered photon energies. Applying the formula, the energy resolution due to the statistical fluctuation for electrons stopped inside the silicon microstrip detectors varies from 1.3 percent at 100 keV to 0.75 percent at 350 keV. The electronics noise of the detector is about 2 keV. Therefore the total energy resolution is dominated by the electronics noise which is the same for both the converter and the calorimeter.

The angular resolution is calculated with an energy resolution of 2 keV (FWHM) where $\Delta\theta$ for forward scattered gamma rays (i.e., $\theta<90°$) varies from 5° at a $\theta$ of 30° to about 3.2° at a $\theta$ of 70° for 141 keV $^{99m}$Tc incident photons. The same calculation carried out for 364 keV $^{131}$I gamma rays gives angular resolutions of approximately 1° for a $\theta$ of between 20° and 90°. Thus the angular resolution improves significantly with an increase in the photon energy. Also the effects of amplifier noise are reduced as more electron-hole pairs are created by higher energy scattered electrons. At a distance of 20 centimeters these angular resolutions produce effectively 6 to 3.5 millimeter spatial resolutions for 141 keV gamma rays and 3.5 to 1.5 millimeter spatial resolutions for 364 keV gamma rays. At a distance of 2.5 centimeters the same energy gamma rays produce 2.2 to 1.4 millimeter spatial resolutions and 0.4 millimeter spatial resolutions, respectively.

The geometric angular resolution, $\Delta\theta_{Geom}$, is the FHWM variation of the axis of the image cone and is dependent upon the silicon microstrip detector pixel size and the distance between the first two scatters. The FWHM value can be calculated similar to that for a collimator. Normally the geometric angular resolution is kept much smaller than the scatter angle variation which depends strongly on the energy resolution as shown above. It is easier to adjust the geometric angular resolution in a silicon microstrip detector as the pixel dimensions can be as small as 25 microns. The pixel size for the simulated model is 1 square millimeter.

Another important advantage of silicon microstrip detectors is that they do not need high voltages or cooling to low temperatures. Room temperature functionality is important to produce small size, low cost, and low power detectors. They also have a strong potential for mass production. However, a significant number of wafers are needed to achieve the conversion rates required for high sensitivity. Their small thickness and ultrasonic wire bonding capability render them good candidates for compact printed circuit board mounting with data acquisition ICs placed next to them. The readout ICS are preferably designed to give fast trigger outputs when events occur and output the address and the analog content of the channel that has the data.

Figure 5:
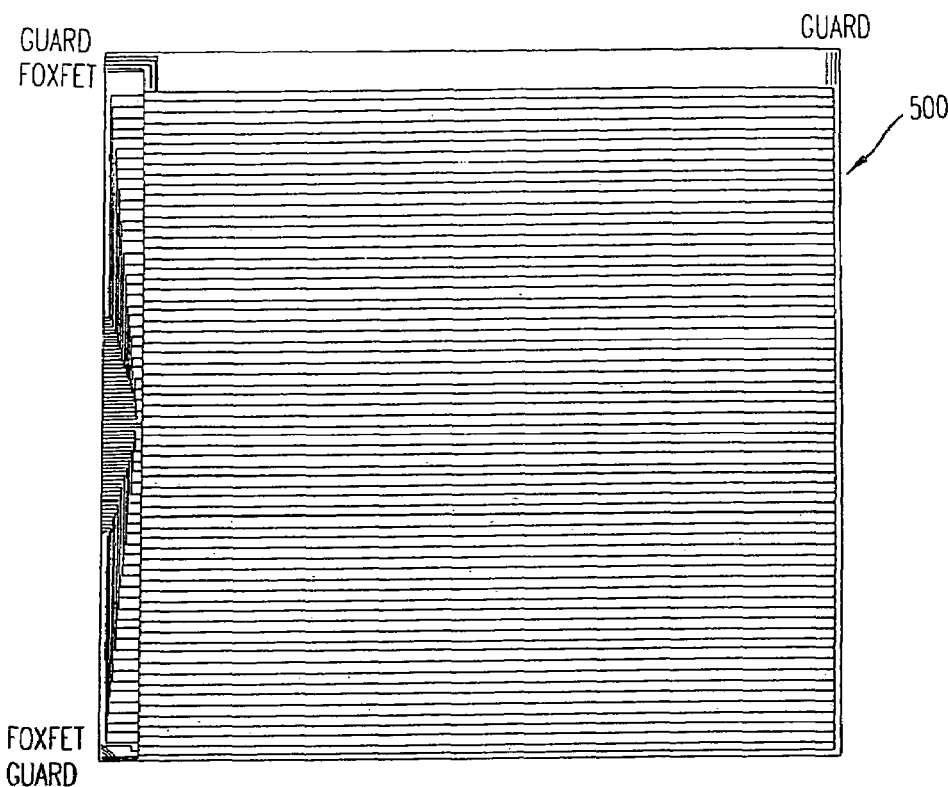
FIG. 5 is an illustration of one side of an individual double-sided silicon strip detector design.

The schematic details of one embodiment of the individual double-sided silicon microstrip detectors of the present invention are shown in FIG. 5. The design includes a 64 pad output on both junction and ohmic sides, fanned in to 250× 250 micrometer linear pad array, Fan-in connection dimensions are minimized but not to the extent that performance is comprised. As viewed from one side, the opposite side is an exact copy, rotated once by 90°.

Figure 6:
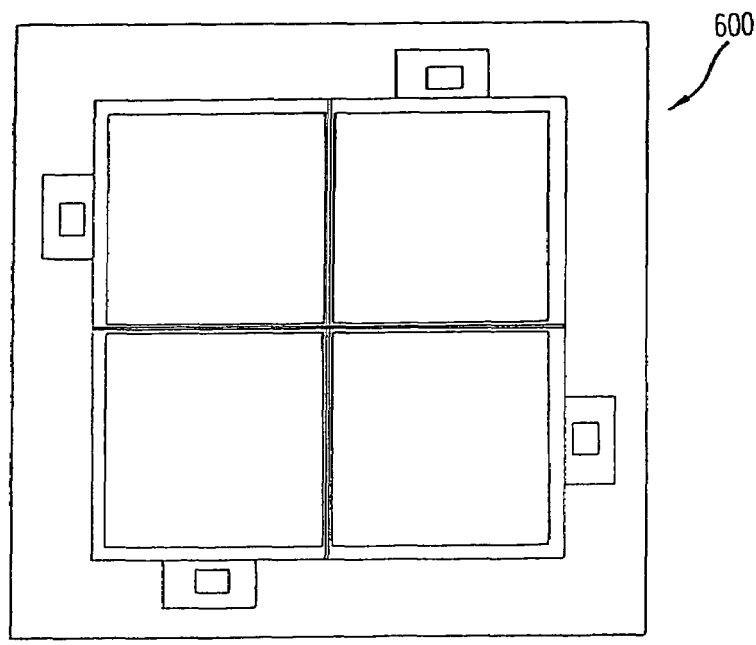
FIG. 6 is an illustration of a silicon microstrip detector module that includes four silicon detector arrays, a PC board, four front mounted FEE chips, and a ceramic chip carrier.

Preferably silicon array 500 is exactly square so that it may be rotated and used in the three other locations on the detector module board to form a detector plane 600 as shown in FIG. 6. The number of guard rings are preferably set to 3 with a pad placement preferably located toward the outside so that they are neighbors when the silicon is rotated.

Preferably a multichannel front end electronics (FEE) chip with self trigger output is mounted onto a ceramic carrier along with the buffer electronics, Although the FEE chip is described briefly below, a detailed description of the FEE chip is provided in U.S. Pat. No. 5,696,458, issued Dec. 9, 1997 and in co-pending U.S. patent application Ser. No. 08/866, 117, filed Jun. 27, 1997, both disclosures of which are incorporated herein for all purposes.

In at least one embodiment, the silicon detector output pads are bonded to 64 input pads on the PC board that support both the silicon strip detectors and the FEE chips. The ceramic FEE chip carrier is bonded onto the PC board pads. The FEE chip is bonded to the pads on the ceramic carrier. Additional detectors can be placed onto a PC board and connected to readout electronics to achieve large effective areas. Alternately, the strips can be daisy chained to decrease the number of readout electronics chips needed.

The above-described mounting technique allows the fabrication of the extremely fine fan-in with the approximately 50 micrometer pitch required at the detector input side on the ceramic carrier. Although such high resolution traces cannot be made easily on a PC board, they can be fabricated on a ceramic substrate.

Figure 7:
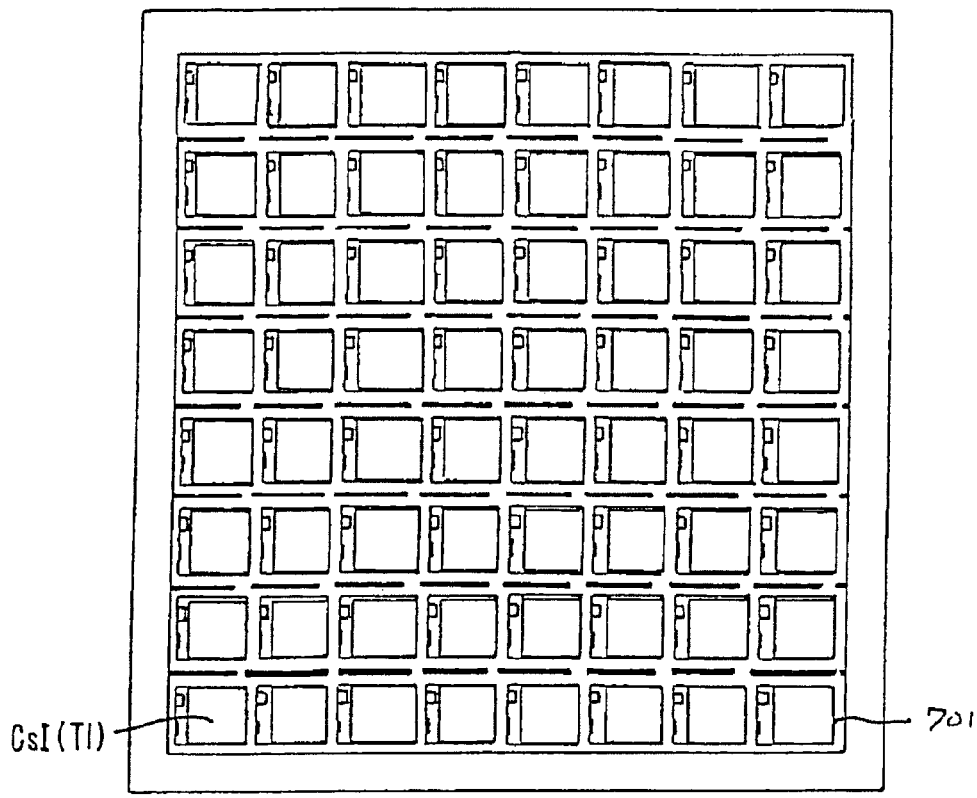
FIG. 7 is an illustration of a top view of a CsI(Tl)/photodiode calorimeter module design according to one embodiment of the invention.
Figure 8:
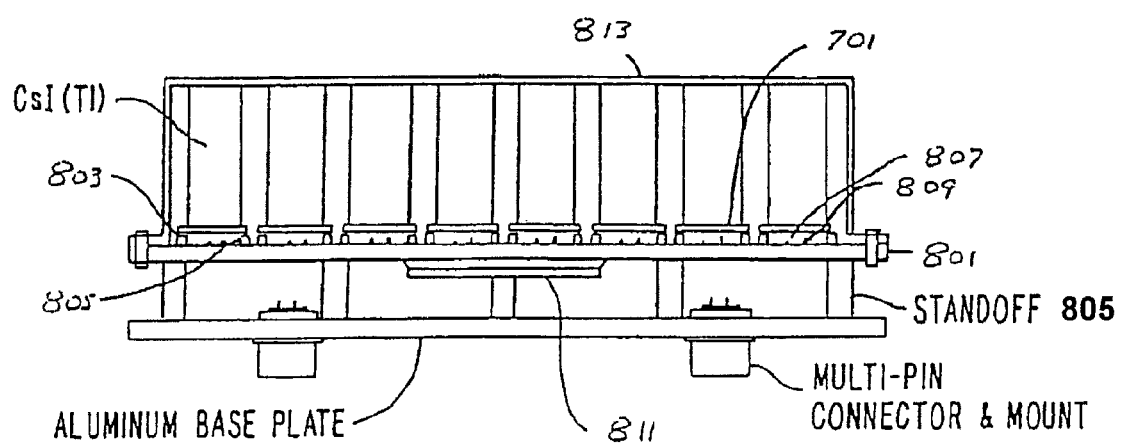
FIG. 8 is a cross-sectional view of the design illustrated in FIG. 7.

FIGS. 7 and 8 illustrate an embodiment of the invention utilizing surface mount technology (SMT) to mount the photodiode by surface mount connectors on one side of the board. By mounting the FEE chip and the diode array on the same board, the length of the connections are minimized thereby lowering the electronic noise. Due to the density of diode pins, the through-hole design prevents the FEE chip to be mounted on the other side of the board, thus making SMT useful.

As shown in FIGS. 7 and 8, the array comprised of diodes 701 is elevated from board 801 by SMT connectors 803 and standoffs 805. Due to the elevation of diodes 701, the surface mounted bias resistors 807 and coupling capacitors 809 can be mounted underneath the diodes. The other side of the board is used to mount FEE chip 811 as well as various other analog components and the by-pass filter network. A plastic housing 813 is placed on the calorimeter printed circuit board to protect the CsI(Tl)/photodiode array from mechanical and humidity damage. This housing also provides improved heat dissipation from the electronics on the other side of the printed circuit board. Preferably the whole silicon hodoscope and CsI(Tl) calorimeter is sealed as a unit.

Figure 9:
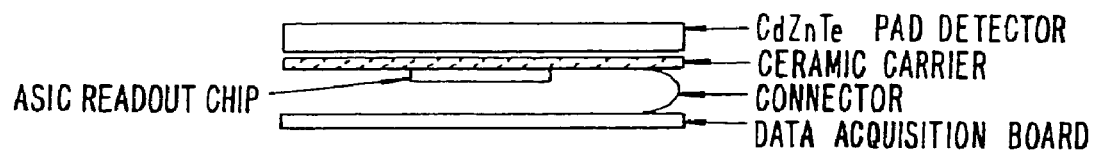
FIG. 9 is an illustration of the side view of an embodiment of a single module of a two-dimensional detector module utilizing CdZnTe pad detectors.
Figure 10:
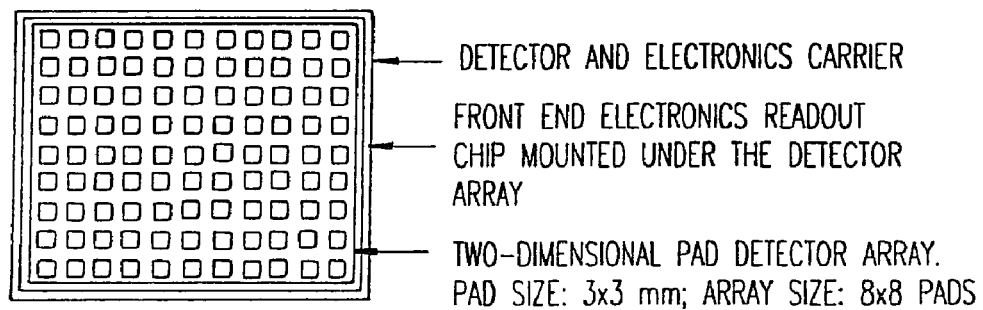
FIG. 10 is an illustration of the top view of the detector module illustrated in FIG. 9.

The above-described design can also be applied to other kinds of position sensitive solid state detectors such as CdTe, CdZnTe, $HgI_2$, HPGe, GaAs, BGO, $CdWO_4$, CsF, NaI(Tl), CsI(Na), CsI(Tl), $PbI_2$, etc. The position sensitive detector modules can be made by mounting individual units on the detector module as shown in FIGS. 7 and 8, or the detector itself can be position sensitive (i.e., single or two-dimensional arrays of pads or pixels) and one or more of these detectors can be mounted together onto the calorimeter module board. Although a two-dimensional 8 by 8 array is shown in FIGS. 7 and 8, the pixel dimensions can be of any size or form. A possible two-dimensional combination of CdZnTe pad detectors is shown in FIGS. 9 and 10. These detectors can also be made with negligible dead perimeter area so that they can be abutted to form uniform large area two-dimensional arrays.

Calorimeter

In at least one embodiment of the invention, a calorimeter is placed around and at the bottom of the silicon microstrip detectors in order to absorb the escaping Compton scattered photons. A variety of different high density radiation detectors can be used. Many of these detectors are relatively high cost (e.g., HPGe, BGO, $CdWO_4$ and CsF) and several require cooling to liquid nitrogen temperatures (e.g., HPGe).

Sodium Iodide is the most popular high density scintillator. It has a large light yield and its response to electrons and gamma rays is close to linear over most of the significant energy range. The NaI(Tl) crystal is fragile and hygroscopic and therefore must be handled carefully and hermetically sealed. It has long decay time and is not suitable for fast timing applications.

Cesium Iodide is another alkali halide that has gained substantial popularity as a scintillator material. It is commercially available with either thallium or sodium as the activator material and has significantly different scintillation properties with thallium. CsI has a larger gamma ray absorption coefficient per unit size and is less brittle than NaI. The two forms of CsI scintillators, CsI(Na) and CsI(Tl), are discussed separately below.

CsI(Na) has an emission spectrum similar 1 o NaI(Tl). Its light yield is also comparable. CsI(Na) is hygroscopic and must be hermetically sealed. Therefore, CsI(Na) is similar to NaI(Tl) and has the same draw backs.

CsI(Tl) is different than NaI(Tl) and has unique properties. It is also only slightly hygroscopic. Energy resolution of 5 percent FWHM at 0.662 MeV has been obtained with 2.5 centimeter diameter by 2.5 centimeter thick CsI(Tl) scintillation crystals coupled to large area (e.g., 2.5 centimeter diameter) mercuric iodide photodetectors. This is about 50 percent better than the NaI(Tl) detectors. The mercuric iodide photodiodes are not yet available as commercial devices. Resolution of 6 percent at 0.662 MeV has been obtained for considerably smaller CsI(Tl) crystals using avalanche photodiodes. Large area PIN diodes coupled to 1 centimeter by 2 centimeter CsI(Tl)crystals give a 7 percent resolution at 0.662 MeV. These crystals produce 35 percent more photons per MeV than NaI(Tl) and their light spectrum is much better matched to the sensitivities of the photodiodes. A key to improved energy resolution is good light collection by matching the areas of the crystals to those of the photodiodes.

An important property of CsI(Tl) is its variable decay time for different particles. Therefore pulse shape discrimination techniques can be used to differentiate among various types of radiation such as electrons, protons and alpha particles. The CsI(Tl) light output is quoted lower than NaI(Tl) for bialkali photomultiplier tubes (PMTs). The scintillation yield is actually found to be larger than that of any other scintillator because its light emission peaks at longer wavelengths. It can be used with photodiodes with extended response in the red region of the spectrum. Its energy resolution is equal to or better than the energy resolution of the NaI(Tl) crystals. For these reasons CsI(Tl) crystals are used in at least one embodiment of the invention.

CdTe, CdZnTe, HPGe and $HgI_2$ are solid state detectors and can be made in arrays for position sensitive applications. They are high Z and high density crystals. They are used to detect x-rays and gamma rays directly without need for photomultiplier tubes or PIN and avalanche photodiodes. They produce much better energy resolution than the other detectors which require photomultiplier tubes or PIN and avalanche photodiodes since they convert the energy deposited by the x-ray and gamma ray photons into light, not electron-hole pairs.

High purity germanium (HPGe) offers extremely high energy resolution and exhibits excellent gamma ray absorption properties, making it the detector of choice for high accuracy spectroscopy. Unfortunately since it only works at liquid nitrogen temperatures, bulky refrigeration systems are required which further increase the cost of this detector. HPGe is available in single small crystals and works by collecting the electron hole pairs produced inside the crystal similar to the silicon detectors and does not require PMTs. Because of the large cost this detector is mainly used for applications which require ultra high energy resolution and small size detectors.

BGO, $CdWO_4$ and CsF are excellent high density and high Z scintillators. They have lower energy resolution and light output. Their maximum light emissions peak around 430 nanometers, similar to NaI(Tl), and require PMTs for detection. $CdWO_4$ and especially CsF have shorter decay constants and faster rise times than the others and can be used for timing. However, since the preferred detector of the present invention does not use time-of-flight to determine the direction of the scattered gamma ray photon, good time resolution is not important.

The preferred room temperature detector for the calorimeter of the present invention is CdTe or CdZnTe. These detectors are described in more detail below.

Data Acquisition System

As noted above, an important technological requirement for the present invention is the FEE chip with self trigger output to readout the silicon strip and calorimeter detectors. In order to provide a readout chip with a trigger output capability, comparators can be incorporated into the readout chip to detect a strong signal above the externally set threshold and the outputs of the comparators can be fanned in using a fast OR circuit to produce the single trigger output.

Figure 11:
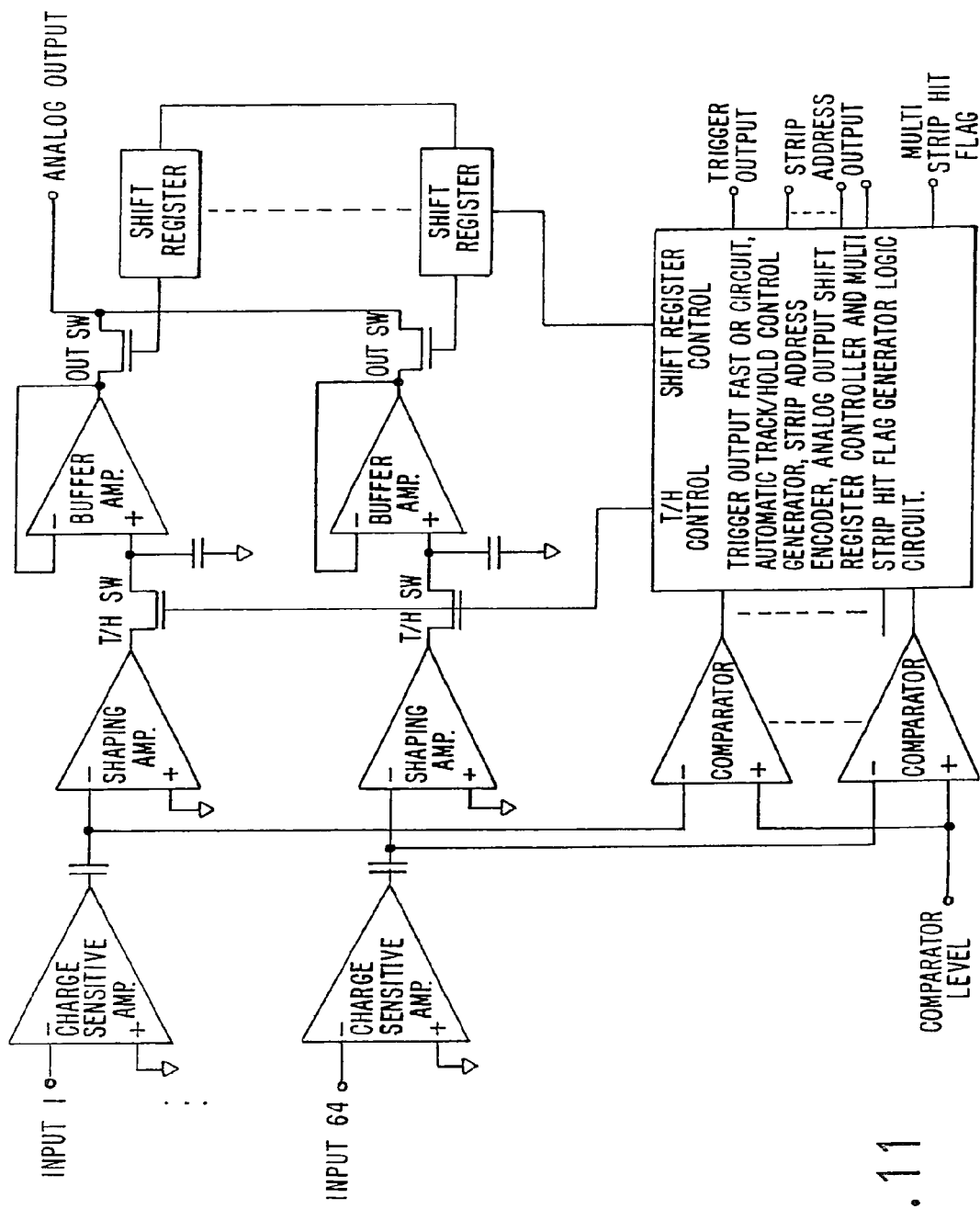
FIG. 11 is a schematic diagram of a possible multi-channel silicon microstrip detector readout chip with fast data readout and trigger output capability.

The preferred FEE chip is a 64 channel, charge sensitive, mixed signal ASIC CMOS chip, a version of which is illustrated in FIG. 11. If desired, similar chips with fewer or greater numbers of inputs (e.g., 16 or 32 inputs) can be used based on the same design. Each channel of the chip consists of an analog section and a digital section. The input from the silicon strip detector is directly coupled to a low noise, charge sensitive amplifier. The outputs of the charge sensitive amplifier are connected to a shaper amplifier. The time constant of the shaper amplifier is typically on the order of 100 nanoseconds although other time constants (e.g., 1 microsecond) may also be used depending on the embodiment of the invention. The output of the shaper amplifier goes into the track and hold (T/H) switch. The T/H switch can be controlled externally or activated internally from the trigger output with a delay set to turn on the hold at the peak of the shaped pulse. The T/H switch is connected to the input of the buffer amplifier through the voltage following capacitor. When the T/H switch is open the voltage on the capacitor is held constant and the voltage level is buffered on to the analog output switch. A shift register connects each buffer output to the single analog output pin in sequence, from input 1 to N, by an external clock input. The shift register also has an external clear input to reset it and a clock output to daisy chain it to other readout chips. Only one clock input is sufficient if the clock outputs are connected in serial to the clock inputs of the adjacent readout chips. The charge sensitive amplifier outputs can be fanned out to comparators with a common external level adjustment. The outputs of the comparators can be fanned in through a fast OR circuit which will produce a trigger signal if any comparator input exceeds the set threshold. The trigger signal can also be used with a suitable delay to control the T/H switches to apply hold signal at the peak of the pulse from the shaper amplifier.

The data acquisition speed of the readout chip can be increased using the extra versatility introduced by the comparators. The design shown in FIG. 11 does not tell which strip has the information so all strips are readout to find the strip that has the signal. A logic circuit can be added to the design which detects the channel with the largest signal from the comparator outputs, applies a track and hold signal, and connects the strip with the signal to the analog output pin. At the same time it can encode the address of the strip that has the information and output it as the address of the strip with the signal. There could be an occasional signal on more than one strip, Multi-hits can be detected and an output can be generated to warn of a multi-hit signal. The trigger signals are generated for each readout chip. They have to be externally processed for the hodoscope in coincidence with the calorimeter to produce the single trigger signal to activate the data acquisition system. For extremely high signal rates this may not be possible. In such a case each wafer or front end readout chip can be separately readout in parallel using independent data acquisition electronics and tagging each event time by using an accurate clock. The calorimeter crystals are also individually readout and event times tagged by the same clock. Since the calorimeter is running at much slower speeds, individual readout modules are not necessary and can be readout in groups.

The data readout can be carried out in parallel and can be stored on-board using individual module memory. This is the key to achieve fast data throughput rates. The data can be asynchronously accessed by the host computer, analyzed and displayed on screen in real time. Data acquisition rates of 1 to 10 MHz per readout chip (or silicon wafer) are achievable.

Figure 12:
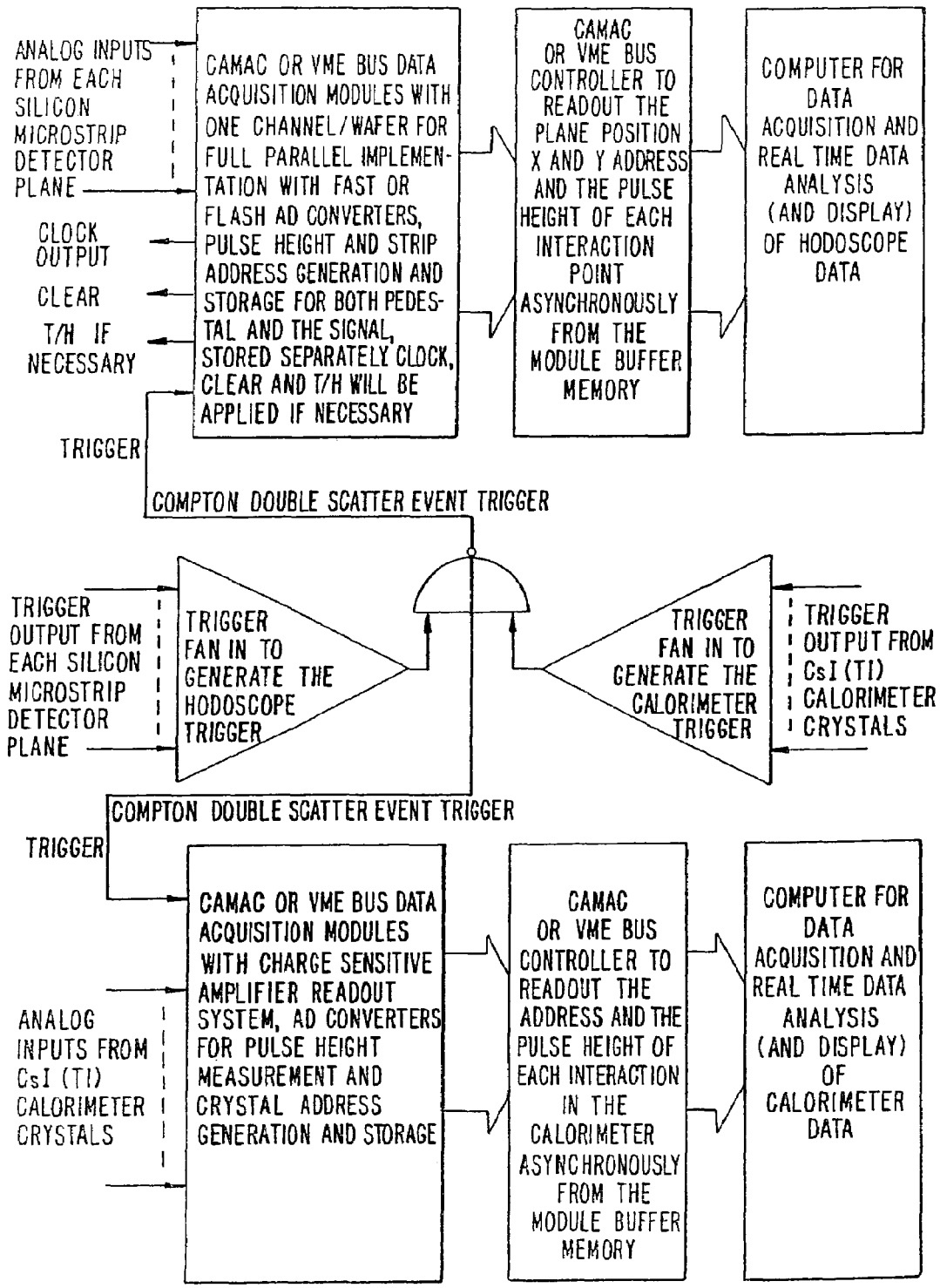
FIG. 12 is a block diagram of a real time data acquisition system for use with the present invention.

A block diagram for a possible readout electronics system is shown in FIG. 12. The electronics has two similar sections for the hodoscope and the calorimeter readout. A true event is a coincidence between the hodoscope and the calorimeter. Since most of the time both sides observe more than a single interaction, a fan-in system is used to convert the several trigger signals into one master trigger. The fan-in can be designed to recognize a track with adjacent planes producing the signal and to reject random coincidence events.

The two master trigger signals from the hodoscope and the calorimeter are sent to a coincidence unit to create the Compton double scatter event trigger. The Compton double scatter trigger signal is only generated if there is a master trigger signal from both the hodoscope and the calorimeter. This is the arrangement which does not employ the time tagged data readout method.

The Compton double scatter event trigger activates data acquisition for both the hodoscope and the calorimeter simultaneously. CAMAC, Fastbus, VME, or VXI bus modules can carry out the data acquisition. The CAMAC system is the most cost effective. The custom designed data acquisition modules for the hodoscope produce the necessary microstrip readout chip control electronics such as the T/H (if not generated internally in the readout chip), a clear signal to reset the shift registers, and the clock pulse to multiplex each strip to the analog output.

The analog input channels from different hodoscope planes are read out synchronously with the clock pulse output. The module converts the pulse height information received from the analog output pin to a digital number. In parallel with reading the hodoscope data, it also digitizes the signal(s) from the calorimeter. Immediately after reading out the last signal it clears the hodoscope to reset the readout chip so that it can receive the next event. It is assumed that the analog output of each readout chip in each detector plane is fanned-in to allow a single signal to be sent to the readout module. It is also possible to design a microstrip readout chip that can internally connect the strip which has the maximum signal to the analog output and also produce the encoded address of the strip. In such a case the clock output will not be necessary and the silicon microstrip detectors can be readout asynchronously at a much faster rate.

The custom made CAMAC, Fastbus, VME, or VXI modules are connected to the bus or crate controllers which are standard devices and available off the shelf. The controllers connect the modules to the data acquisition computer. Depending on the data rate and readout overhead, single or separate computers can be used to read the hodoscope and the calorimeter. The computer stores data on a hard disk, optical drive, or nonvolatile RAM depending on the application. If the data acquisition overhead is not high then one of the computers can analyze the data in real time or a separate computer can access the storage media asynchronously. The results of the data analysis are imaged onto the field-of-view through a display system in real time.

Data Analysis

For each gamma ray detected by the first and second generation Compton double scatter detectors, an "event ring" on the sky containing the source direction can be measured. The half-angle of the cone, as illustrated in FIG. 2, is the Compton scatter angle, $\theta$. The overlap of the rings gives the source direction. The angular resolution is the angular width of the ring. This angular resolution depends on the energy resolution in the hodoscope and the calorimeter as well as the geometric uncertainty in the scattered photon direction. Measuring the recoil electron direction in the Compton double scatter detector reduces the event ring to an arc centered on the source direction as illustrated in FIG. 2. It significantly reduces background and provides a true imaging capability for Compton detectors. The event arcs produces dramatic improvement on the signal to noise ratio compared to event rings. The data analysis methods discussed below can be applied to both types of data.

True imaging is achieved by determining the x and y coordinates of the interactions in the first two planes of the Compton recoil electron track in the silicon microstrip hodoscope. With both the electron and scattered gamma ray directions known and their energies measured, a unique direction is found for each event.

Many different data analysis methods can be applied to the data of the detection system. Depending upon the application, the applied data analysis techniques may closely resemble those used in medical Computer Assisted Tomography (CAT) imaging. This type of imaging is based on the Radon transform and back projection techniques and is standard in the industry. New iterative techniques such as Maximum Likelihood and Maximum Entropy methods can also be applied to enhance the image quality.

Another data analysis technique that can be applied to the Compton double scatter data is the Direct Linear Algebraic Deconvolution (DLAD) technique. One advantage of this technique resulting from its non-iterative approach is that it can produce fast images from the data.

A concise explanation of the DLAD technique is provided below. The reconstruction of the source image from the Compton double scatter data can be represented by the following general formula:

$$D(\chi, \Psi, \varphi, E) = \int_{\chi,\Psi,E} I(\chi_0, \Psi_0, E') R(\chi, \Psi, \chi_0, \Psi_0, \varphi, E', E) d\chi_0 d\Psi_0 dE' + B(\chi, \Psi, \varphi, E)$$

In the above formula, $D(\chi, \psi, \phi, E)$ is the actual Compton scatter data observed by the detector in appropriate coordinates; $\chi$ and $\psi$ are the coordinates of the rectangular image plane; $\phi$ is the Compton scatter angle; E is the energy of the incident photon; $I(\chi_o, \psi_o, E_o)$ is the true image of the source and is not a function of the Compton scatter angle; $R(\chi_o, \psi_o, \phi, E', E)$ is the response function of the detector; and $B(\chi, \psi, \phi, E)$ is the gamma ray background. Normally the calculation is carried out for all energies within the detector sensitivity to determine the total gamma ray flux and for certain energy bands to obtain an energy spectrum. For application to the present invention, the energy spectrum is used to discriminate the scattered photon background. The calculation can also be done for different scatter angle bands, D and I are normally referred to as the data and the image spaces, respectively.

The response function in the DLAD technique is the concentric rings obtained by mapping the scattered photon direction vector in the image plane. This can be used as an ideal detector response function. The true detector response function, R, can be represented by $$R_{i,j,\Phi_s} = \epsilon(E, \theta_j, \Phi_s) \cdot \Delta\Phi_s \cdot PSF \cdot G(\theta_i)$$

where i and j define the bins in the data and image spaces, respectively; $\Phi_s$ is the calculated Compton scatter angle as given by Compton scatter formula; $\epsilon$ is the detector efficiency; $\theta_i$ and $\theta_j$ are the incident zenith angles in data and image spaces, respectively; $\Delta\Phi_s$ is the scatter angle interval; PSF is the point spread function; and $G(\theta_i)$ is the geometric factor. The PSF is the distribution of the scattered photon vectors in the image plane. The PSF can be represented by the two dimensional normal distribution $$PSF = C(\theta_j, \Phi_s) e - \{[(\Phi_t - \Phi_s)^2]/[2\sigma^2(E)]\}$$

where C is the normalization constant determined by the requirement that PSF×$G(\theta_i)$ is equal to 1. The PSF and $G(\theta_i)$ are symmetric in the azimuth, thus giving a two-dimensional image. The present invention can produce three-dimensional images due to the Compton scatter process. Therefore, either two-dimensional image slices parallel to the converter planes are produced or a direct three-dimensional image can be constructed.

The DLAD technique can produce fluctuations on the image space that are due to the geometric factor forcing data space to zero at the corners and edges of the field-of-view where the data may be scarce and the Poisson fluctuations are large. This effect can be improved by applying the positivity requirement. The positivity requirement is based on the fact that in image space one cannot get negative fluxes. The positivity constraint has been introduced into DLAD. The new technique is called Constrained Linear Algebraic Deconvolution (CLAD).

System

Figure 13:
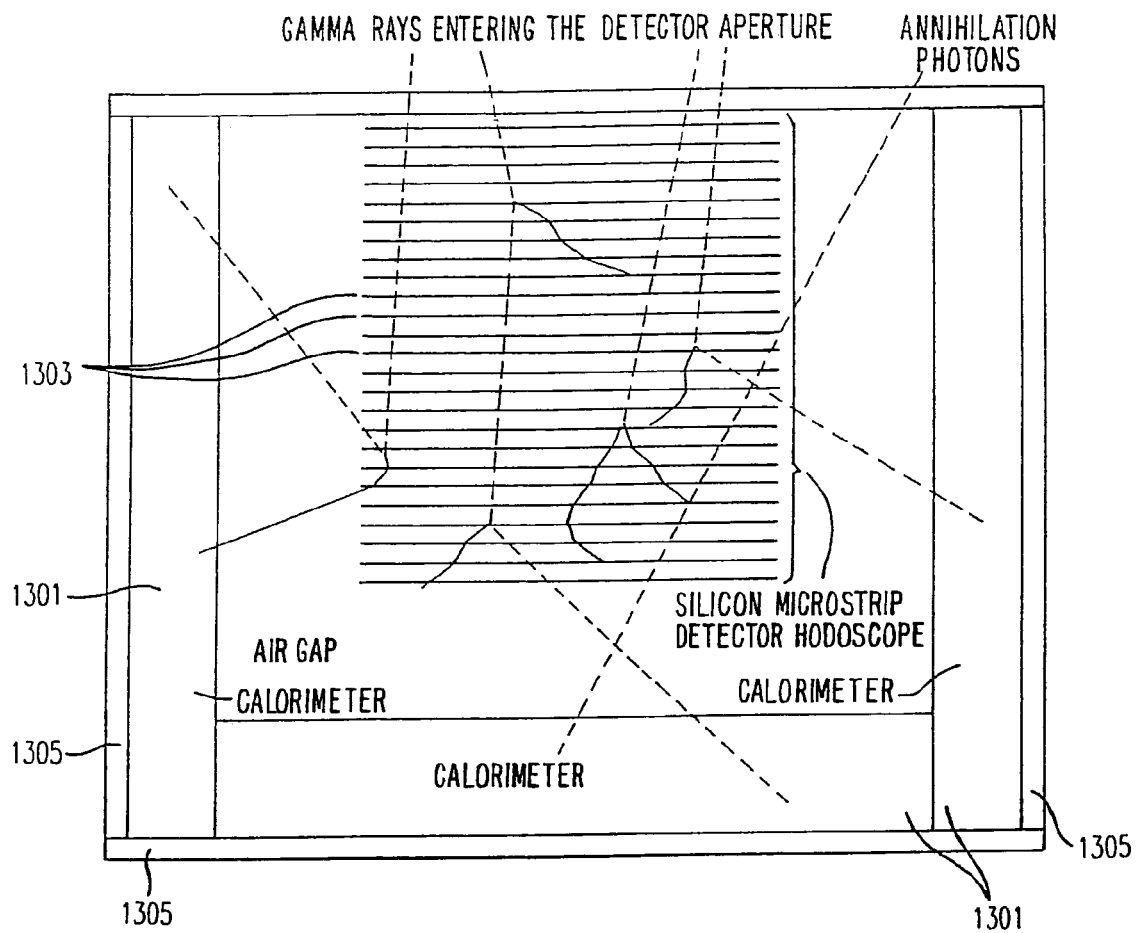
FIG. 13 is an illustration of the cross-section of the detection system according to one embodiment of the invention.
Figure 14:
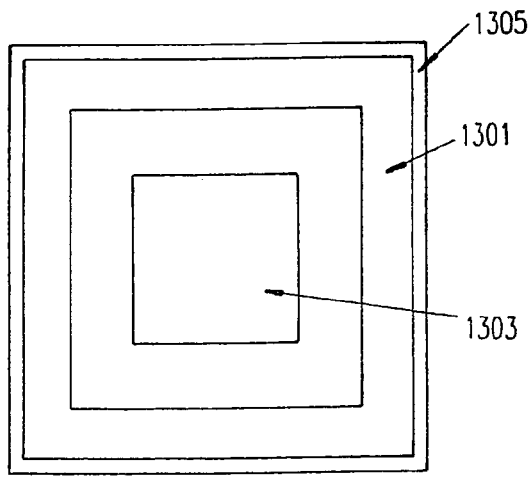
FIG. 14 is an illustration of the top view of the detection system illustrated in FIG. 13.
Figure 15:
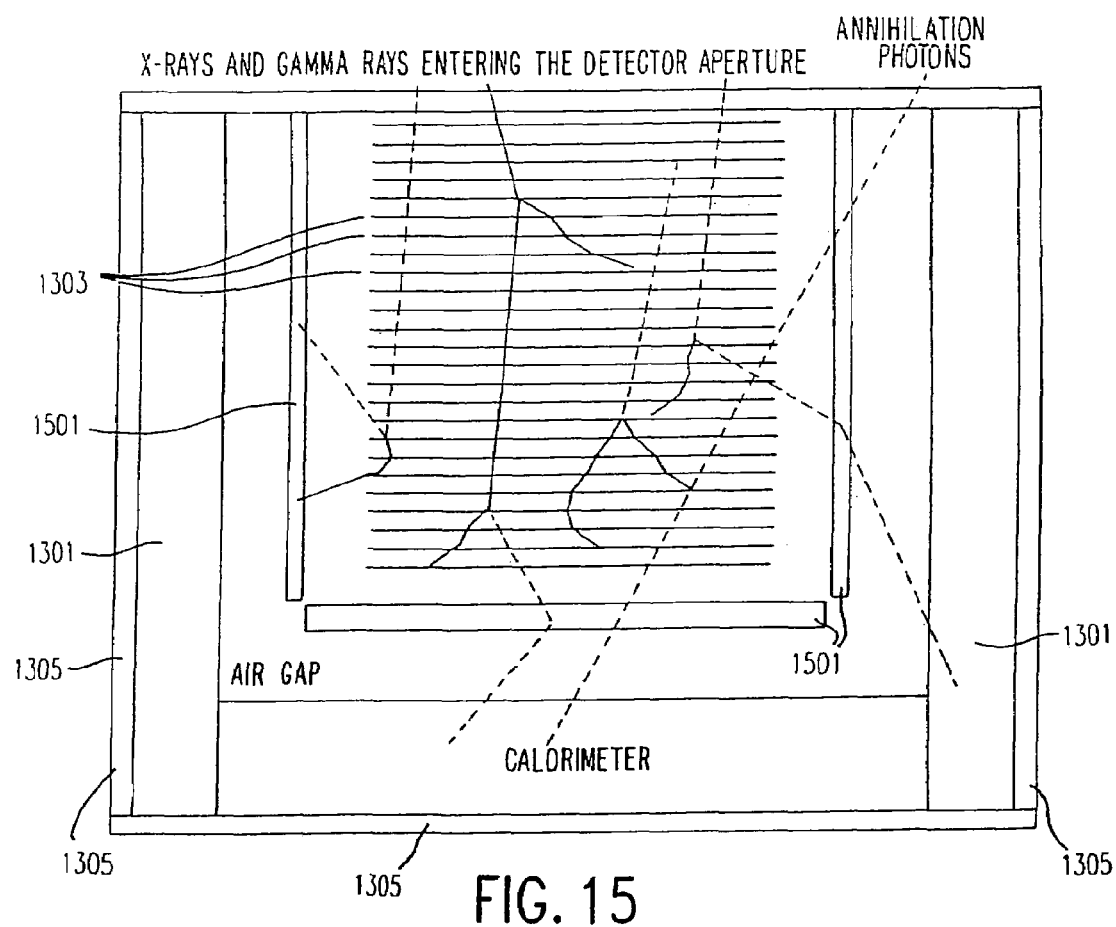
FIG. 15 is an illustration of the cross-section of a detection system similar to that shown in FIG. 13 which includes an additional detection level.
Figure 16:
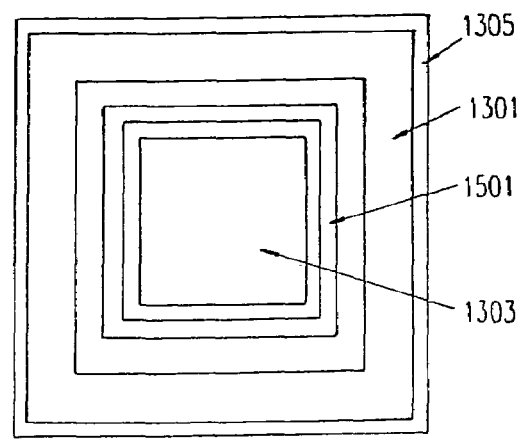
FIG. 16 is an illustration of the top view of the detection system illustrated in FIG. 15 utilizing a square cross-section.
Figure 17:
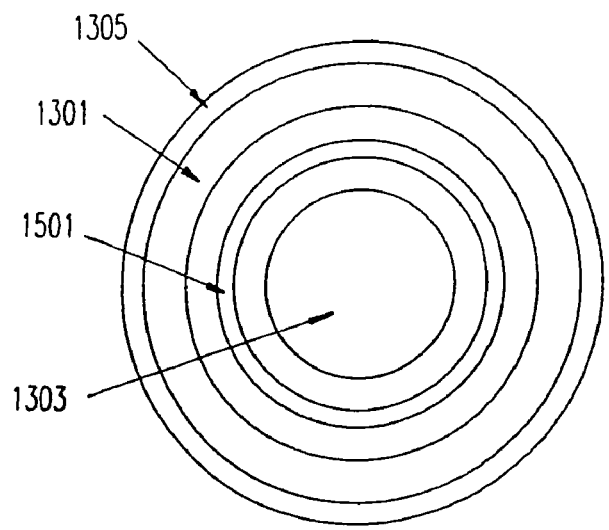
FIG. 17 is an illustration of the top view of the detection system illustrated in FIG. 15 utilizing a cylindrical cross-section.

FIGS. 13 and 14 illustrate the cross-section and a top view, respectively, of one embodiment of the invention. In this embodiment, a calorimeter 1301 surrounds a hodoscope comprised of between approximately 1 and 100 silicon strip detector planes 1303, and preferably between approximately 10 and 25 planes 1303. Calorimeter 1301 is shaped to detect the large angle Compton scattered photons. FIGS. 15-17 illustrate a variation on this embodiment which includes a middle detector layer 1501 between the hodoscope and calorimeter 1301. Detector layer 1501 is made of position sensitive x-ray and gamma-ray detectors.

Preferably detector layer 1501 has a thickness of approximately 0.1 millimeters to 1 centimeter. This layer performs two functions. First, it increases the energy and angular resolutions for the lower energy x-rays and gamma rays which will primarily be stopped within this layer. Second, it allows for three level scatter instead of two, thus providing more information on the incident photon. For example, the total energy and direction of the incident photon can be determined even if the photon makes a Compton scatter in the calorimeter and escapes.

The silicon microstrip detectors 1303 preferably have a thickness of between 200 and 300 micrometers, the selected thickness being dependent upon the desired performance as well as the availability of the detectors. Preferably detectors 1303 are double-sided with approximately 1 millimeter pitch strips orthogonal to each other on the two sides. In order to achieve the desired detector plane area, each detector plane 1303 is preferably comprised of four individual detectors 1801 bridged together to form a square plane of approximately 100 square centimeters as illustrated in FIG. 18.

Figure 18:
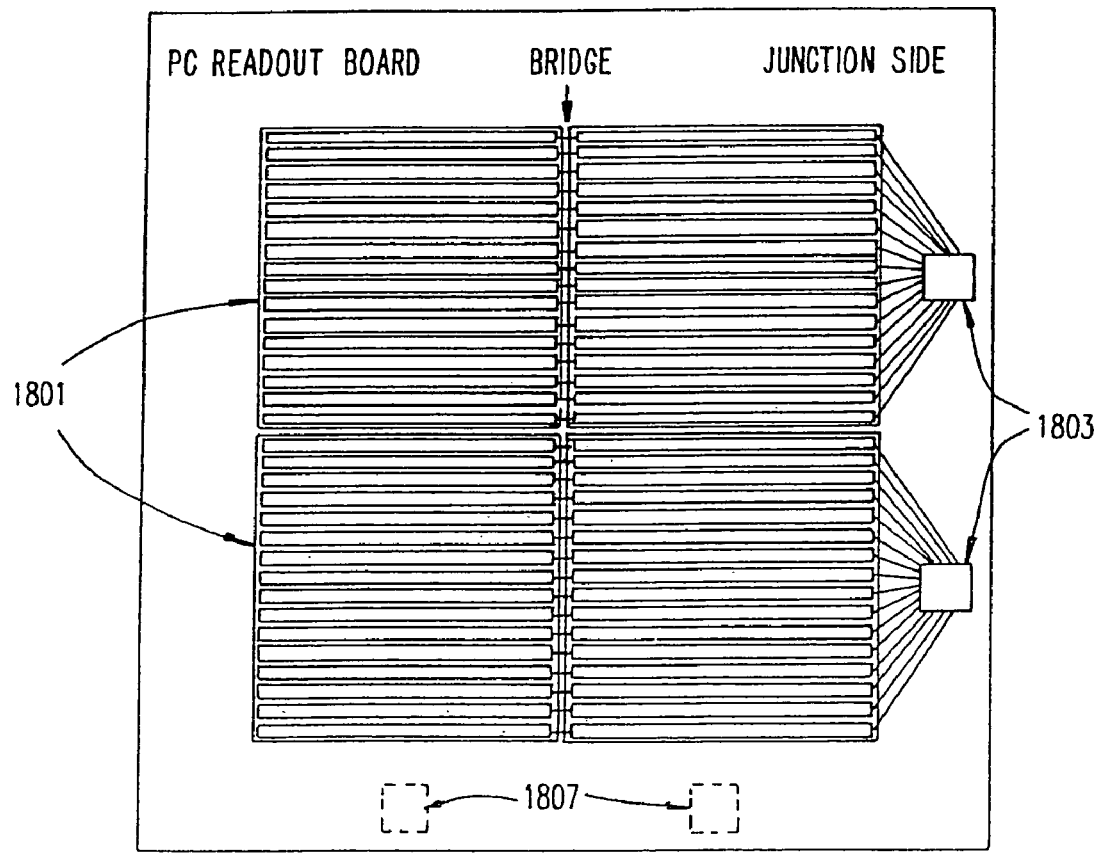
FIG. 18 is an illustration of a hodoscope detection plane utilizing four bridged double-sided silicon microstrip detectors.

Bridging detectors as illustrated in FIG. 18 decreases the readout channel number and related electronics significantly. Preferably ultrasonic bonding is used to form the bridges and to connect them to readout chips 1803. Readout chips 1803 are mounted as near as possible to detectors 1801 in order to minimize the size of front end PC readout board 1805. The fan in from the detector strips to readout chip pins are preferably gold plated for good quality ultrasonic bonding.

FIG. 18 shows the junction side of board 1805. The strip detectors on the ohmic side (i.e., the back side) of board 1805 run orthogonal to the junction side so that both the x and y dimensions of an interaction in the silicon are measured simultaneously. The bridging on the ohmic side is similar to the junction side with the position of ohmic side readout chips 1807 preferably being mounted on the reverse side of board 1805. The output and control signals for the readout chips are not shown as they depend on the chip design.

Figure 19:
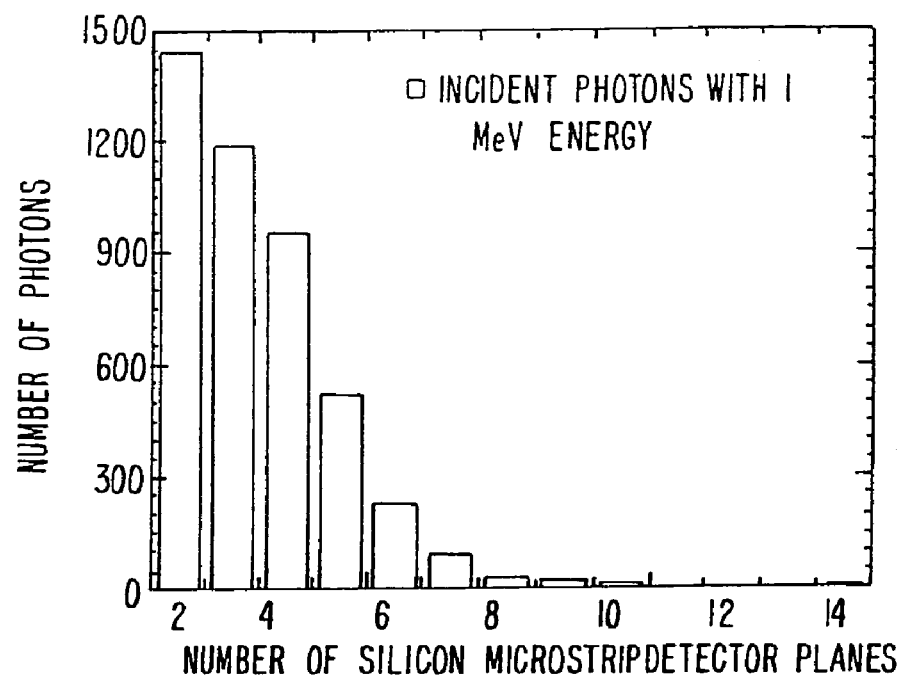
FIG. 19 is a graph of recoil electron track length distributions in a silicon hodoscope for 1 MeV gamma rays.
Figure 20:
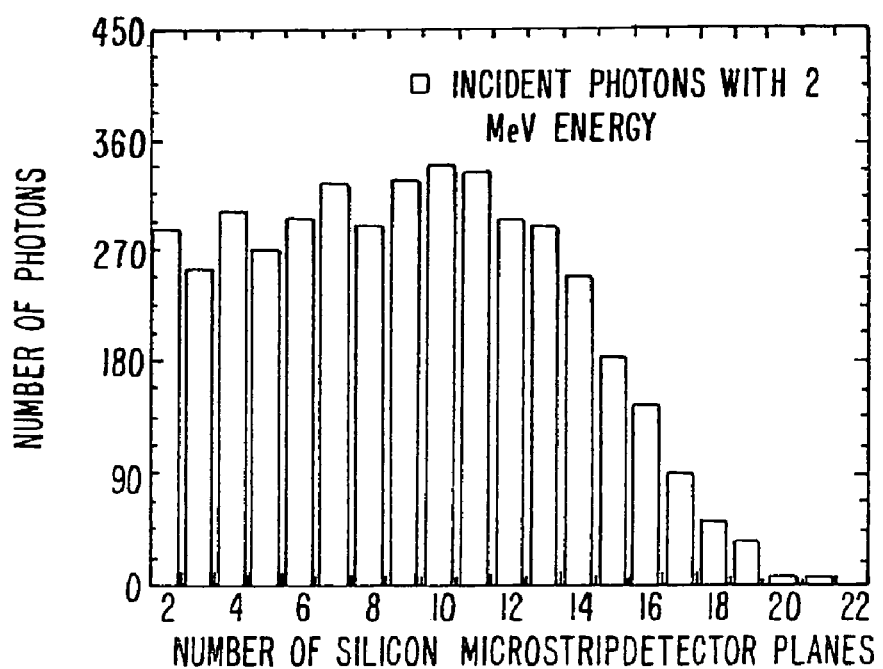
FIG. 20 is a graph of recoil electron track length distributions in a silicon hodoscope for 2 MeV gamma rays.

A simple Monte Carlo calculation using MCNP software was performed. FIGS. 19 and 20 provide the track lengths for incident photon energies of 1 and 2 MeV, respectively, assuming 200 micrometer thick detector planes. For 1 MeV gamma rays the recoil electron traverses an average of 3 detector planes. This increases significantly as the energy of the incident photon increases. For 2 and 6 MeV gamma rays an average of 8 and 25 detector planes are traversed, respectively. Depending upon the number of silicon detector planes, typically the recoil electrons with long tracks will escape the hodoscope and enter the calorimeter. This effect does not present a problem since the missing energy of the recoil electron in the hodoscope is recovered by adding the energy deposited in the calorimeter, thus allowing the event to be fully determined.

Figure 21:
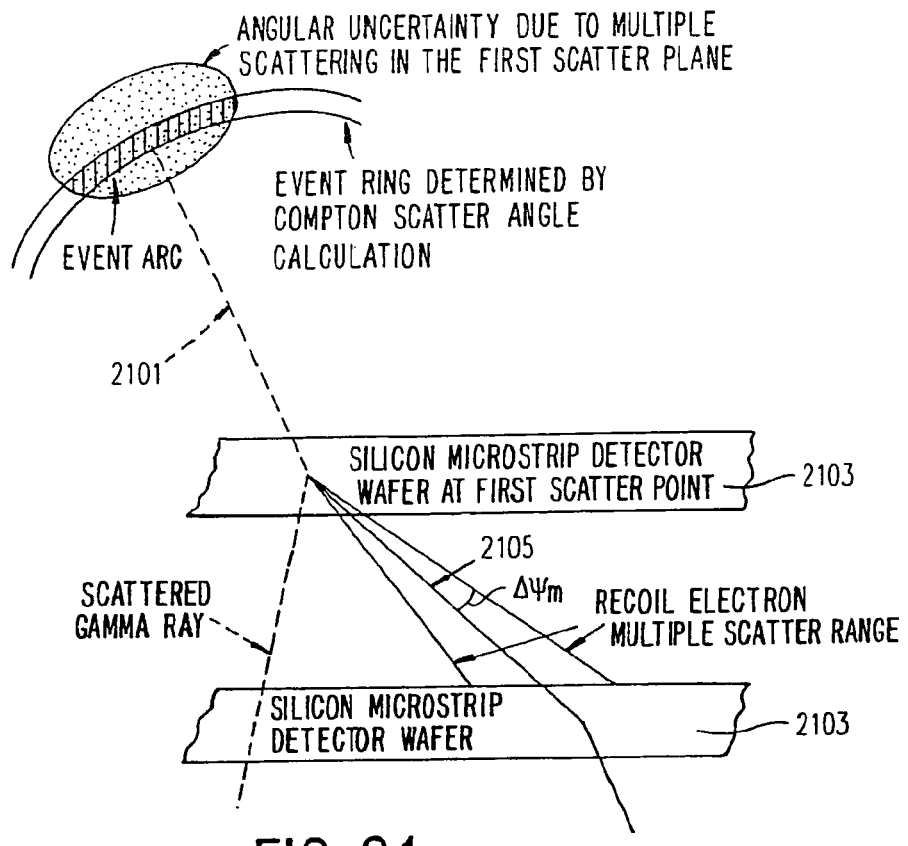
FIG. 21 is an illustration of a multiple scattering event in which the multiple scatter angles along the electron track can be used to determine the direction of motion of the electron.

FIG. 21 illustrates the multiple scatter along a recoil electron track produced through Compton scattering of a 2 MeV gamma ray 2101. As electron 2105 loses energy traversing silicon planes 2101, the deflection in its trajectory increases significantly. Thus the start and end of the recoil electron track can be identified by measuring the deflections in the track at each detector plane.

In a multiple scatter event, the multiple scatter angle, $\theta_0$, is inversely proportional to the momentum and velocity of the particle. The multiple scatter angle increases strongly with the decrease in the momentum and velocity as demonstrated in the simplified formula:

$$\theta_0 = \{[14.1 \text{ MeV/c}]/p\beta\} Z_{inc}\{[L/L_R][1+(1/9)\log_{10}(L/L_R)]\}^{1/2}$$

where $p$ is the momentum in MeV/c, $\beta$ is the velocity, $Z_{inc}$ is the charge number of the incident particle, and $L/L_R$ is the thickness of the scattering medium in radiation lengths. This formula is accurate to about 5 percent for a value of $L/L_R$ between $10^{-3}$ and 10, excluding the cases of very light elements or low velocity particles where the error is about 10 to 20 percent.

The multiple scatter angles can be calculated using the MCNP program which utilizes the more rigorous Moliere theory. There is a large increase in the multiple scatter angles towards the end of the track due to the decrease in the momentum and the velocity of the particle before it stops. At least 4 interactions are required to get the minimum 2 multiple scatter angles per track that are required to determine the direction of motion of recoil electron 2105.

The energy loss suffered by recoil electron 2105 at each silicon detector plane 2103 is not uniform. The energy loss in each detector plane 2103 increases as the kinetic energy decreases, thus the energy deposited in the first interaction plane is normally much lower than the energy deposited in the last plane where it stops. This gives another signature to measure the direction of motion for a recoil electron. The energy deposition of the recoil electron is also calculated by the Monte Carlo program. For high energy relativistic particles, the energy loss in a medium is constant and minimum. Such high energy particles are referred to as minimum ionizing particles. As the particle velocity decreases the energy loss by ionization increases. A minimum of 2 interaction points may be sufficient to apply this method since the energy deposition is a scalar quantity. This allows the determination of direction of motion of recoil electrons even with 2 interaction points, also the minimum required to calculate the direction of the recoil electron to reduce the event ring into an event arc. The formula to calculate the direction of motion factor, F, if there are only 2 or 3 interaction points in a track is given by:

$$F_{2,3} = [E_{Last} - E_{First}]/[E_{Last} + E_{First}]$$

where $E_{First}$ and $E_{Last}$ are the energies deposited in the first and last interaction points, respectively, assuming that the recoil electron is moving into the silicon hodoscope from front to back. The factor F varies from −1 to 1. Positive values indicate that the recoil electron track is progressing from the front towards the back of the detector while negative values mean the opposite is true. The differential scatter angle and energy loss can also be used to determine the direction of motion for the recoil electron.

The factor, F, based on track lengths of at least 4 interactions, is revised to make use of the large differences in the first and last energy deposition values as well as the strong difference between the sum of the first and second halves of the multiple scatter angle distribution. The revised formula is given as:

$$F_{\geq 4} = \frac{E_{Last}\sum_{i}^{SecondHalf}\theta_i - E_{first}\sum_{i}^{FirstHalf}\theta_i}{E_{Last}\sum_{i}^{SecondHalf}\theta_i + E_{First}\sum_{i}^{FirstHalf}\theta_i}$$

where $\theta$ is the multiple scattering angle of the recoil electron at each detector plane and $E_{First}$ and $E_{Last}$ are the energy deposited in the first and last interaction points, respectively. Other techniques can also be used to determine the direction of the recoil electron track.

The interactions of the incident photon in the hodoscope and the calorimeter produce an ambiguity since it is not known whether the photon made a Compton scatter in the hodoscope or calorimeter first. The situation is completely symmetric. If this ambiguity is not resolved then the direction of the background photons incident on the back of the detector can be mistaken for true events incident on the detector aperture. Application of the direction of motion determination described above can resolve this ambiguity since the direction of the incident photon can be derived from the direction of the recoil electron.

The summation is carried out for the first and second halves of the recoil electron track, assuming the track is moving from the front to the back of the hodoscope. Therefore if F is positive, the track is progressing from the front to the back of the hodoscope while if F is negative, the opposite is true. If F is zero, the direction is indeterminate.

The effectiveness of this technique was tested for many tracks of gamma ray of predetermined energy. The results of the calculation for 2 MeV gamma rays showed that about 4 percent of the calculated events are negative and resemble upward moving recoil electron tracks progressing from the back of the hodoscope to the front. This is a small effect and decreases at higher incident photon energies. For example, the tracks mistakenly calculated to be moving backward increases to 11 percent at gamma ray energies of 1 MeV and decreases to 2 percent at 6 MeV.

In the embodiment of the invention illustrated in FIGS. 13-17, calorimeter 1301 is preferably made from CsI(Tl) crystals viewed by photodiodes. The calorimeter can also be built from NaI(Tl) crystals or any other high density scintillator with good characteristics. The calorimeter is formed in the shape of a well surrounding all sides of the hodoscope except the front aperture. The selected calorimeter material as well as the amount of area covered is primarily dependent upon the cost of the scintillator for a given thickness. The high density scintillator also acts as an excellent active shield for background gamma rays.

The position sensitive CsI(Tl) crystal calorimeter is preferably constructed from rectangular bars with a cross-section between approximately 1 square centimeter and over 6 square centimeters and a length varying from 1.5 to 2.5 centimeters. The wide variation of length is due to the energy range of detection. The bottom section of the calorimeter needs longer crystals since the forward scattered gamma rays carry most of the primary photon energy. The CsI(Tl) crystals on the side walls of the calorimeter can be short, as the photons with large Compton scatter angles carry a much smaller fraction of the primary photon energy. Since the Compton scatter angle increases with the height of the calorimeter at the side walls, a tapered crystal length can be used; longer CsI(Tl) crystals can be placed on the walls near the bottom of the calorimeter and the crystal length can be gradually reduced upwards toward the rim.

If desired, for example to reduce the costs associated with the calorimeter, the height of the calorimeter side walls can be reduced to below the top of the silicon hodoscope. This will cause backscattered gamma rays at sufficiently large angles to miss the calorimeter and not be detected. Given that the probability of backscattered gamma rays is lower than that for forward Compton scatters, especially at higher incident photon energies, this loss is negligible for many cases.

Figure 22:
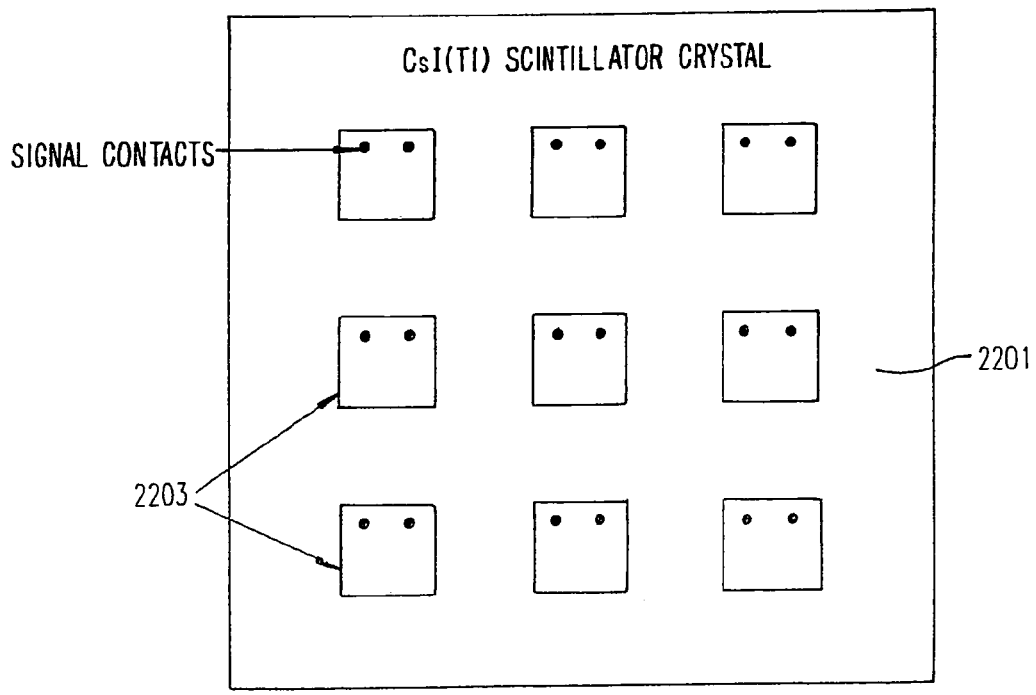
FIG. 22 is an illustration of the bottom of a CsI(Tl) calorimeter using an array of photodiodes to view the crystal.

In this embodiment, the calorimeter is comprised of a mosaic of individual CsI(Tl) crystals where each crystal is individually viewed by a photodiode. As a result of this configuration, the number of photodiodes required is the same as the number of crystals. An alternative method illustrated in FIG. 22 uses flat CsI(Tl) crystals 2201 with sufficient size to cover the bottom and the sides of the calorimeter. Each flat crystal 2201 is viewed by a plurality of photodiodes 2203 placed at equal distance to each other on the back surface of crystal 2201. The position of the interaction point is determined from the centroid of the pulse heights observed by adjacent photodiodes surrounding the interaction point.

Preferably an anti-coincidence shield 1305 surrounds all sides of the detection system as shown in FIGS. 13-17. Shield 1305 is mainly used to veto charge particles such as electrons, positrons and protons incident on the detector from all directions. Charged particles deflect in the Earth's magnetic field and produce a nearly isotropic background. The best low cost material for an anti-coincidence shield is a fast plastic scintillator such as NE-102A with a thickness of between 0.5 and 1.5 centimeters. If an anti-coincidence shield is used, typically the aperture of the detection system uses a thinner scintillator in order to reduce the Compton scatter of gamma rays in the plastic which change the direction of the incident gamma rays. Since the plastic scintillators have low density and low average Z, the Compton scatter probability is very low and a thickness of up to 1.5 centimeters can be used in front of the detector aperture without significant effect. For applications where charge particle background is not significant, shield 805 can be omitted. Furthermore the top hodoscope layer can serve as an anticoincidence shield by requiring that there is no track in this layer in all events that are accepted as x-ray and gamma-ray events.

i) Energy and Angular Resolution

Position resolutions are assumed at the hodoscope to be approximately 1 millimeter by 1 millimeter (i.e., double-sided silicon microstrip detectors with a 1 millimeter pitch) and at the calorimeter of approximately 1 centimeter by 1 centimeter. The calculations were carried out for 0.5, 1, 2, 6, 10, and 25 MeV. Compton scatter angles were not restricted, and threshold energies of 0.05 MeV were applied to the hodoscope and the calorimeter.

The energy resolution of a gamma ray photopeak depends upon the electrical noise, the light collection efficiency, and the intensity spread of the collected light. The electrical noise, however, contributes only a small amount to the full width at half maximum (FWHM) resolution of the photopeak.

When a scintillator is mounted onto a photodiode, the photopeak width increases. The effect of the light collection efficiency from the scintillator results in a much broader peak than with a bare photodiode, For example, the efficiency of light collection from a pulse close to the photodiode surface, near the center of the scintillator, may be significantly different from the collection efficiency when the pulse is from a skewed location. A measured photopeak will be a convolution of all of these results of varying pulse locations. The result is a wide peak. Typical FWHM values even with low electrical noise are about 45 channels. Since both sources of "noise" are independent of each other, the half width at half maximum (HWHM) σ can be written as $$\sigma_{Total}^2 = \sigma_{Opt}^2 + \sigma_{Elec}^2$$

where $\sigma_{Total}$ is the total measured half-width, $\sigma_{Elec}$ is the half-width contribution due to electrical noise, and $\sigma_{Opt}$ is the spread due to the scintillator/photodiode geometry. Since the electrical part and the total part are known from measurements, the optical component can be estimated to be $\sigma_{Opt}^2 = \sigma_{Total}^2 - \sigma_{Elec}^2$. Thus a typical value for a 1.0 by 1.0 by 1.75 cubic centimeter CsI(Tl) crystal is $2\sigma_{Opt} = 40$. This means that the spread in the photopeak has very little to do with the electrical noise performance of the photodiode. That is, with these numbers, it makes little difference if the photodiode noise FWHM is 20 or 22 channels (10% noisier); the total photopeak width would only increase from 45 to 46 channels, causing the resolution to go from 5 percent to 5.1 percent. It also points out that any effort to reduce noise by lowering the temperature will only be beneficial if the noise is reduced by a large fraction.

ii) Effective Area Efficiency Factor and Sensitivity

Untracked events are detected when the Compton scattered recoil electron stops in the same silicon detector in which it is created. In this case the recoil electron direction cannot be measured and the direction of the incident electron is only known as a ring in the field-of-view. If the recoil electron traverses two or more silicon detectors then the incident gamma ray direction is restricted to a short arc in the field-of-view. For incident gamma rays with energies above 1 MeV most of the events are tracked while for incident gamma rays with energies below 1 MeV most event are untracked, assuming silicon detector thicknesses of between 200 and 300 micrometers.

To find the effect of the angle of incidence on the detector efficiency, the response of the detector to gamma rays generated with uniform isotropic distribution must be studied. The results show that the detector efficiency is high for gamma rays entering the detector aperture with zenith angles from 0° to 60°. The gamma rays incident from the side and back of the detector at zenith angles from 90° to 180° have a low efficiency as expected. The efficiency for gamma rays incident from the front of the detector is about a factor of 30 higher than for gamma rays incident from the back.

The sensitivity of this detector is best for incident gamma rays between 1 and 5 MeV. At higher energies the sensitivity is reasonably constant, but there is some loss of sensitivity as the stopping power of the detector decreases with an increase in the energy due to the smaller size of this embodiment of the detector. At lower energies the sensitivity is also reduced as the large angle Compton scattered gamma rays that miss the calorimeter are lost.

iii) Detection of Pair Produced Events

Pair produced events are different than Compton scattered events. The signature of a pair produced event in the present invention is two simultaneous tracks in the form of an inverted V with a single common vertex point in the silicon hodoscope. The dual track is due to the electron-positron pair created in the hodoscope. The inverted V track is accompanied by one or two 0.511 MeV interactions in the calorimeter resulting from the absorption of the 0.511 MeV photon pair created by the annihilation of the positron. One or both of the electron-positron pair can escape the hodoscope and enter the calorimeter. These will be legitimate events and the missing particle energies can be obtained from the calorimeter since the tracks of these particles are already measured and their position of interaction at the calorimeter can be determined. The pair production starts to become important for incident photon energies above 5 MeV.

Examples of System Applications

Figure 23:
FIG. 23 illustrates the use of the present invention for exo-atmospheric mid-course discrimination of nuclear warheads from decoys.
Figure 24:
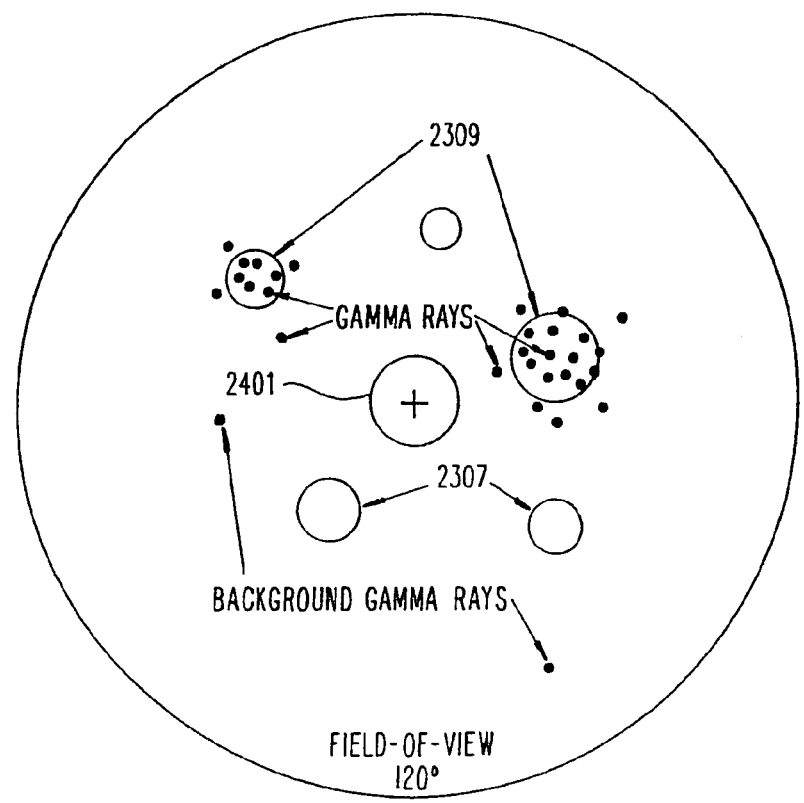
FIG. 24 illustrates the overlay of radar or infrared images with the computer simulation provided by the present invention to discriminate between nuclear warheads and decoys for the application shown in FIG. 23.

As illustrated in FIG. 23, a detection system 2301 according to the above-described embodiment can be mounted within the cone of a scout interceptor missile 2303, i.e., an interceptor missile launched prior to the launch of other interceptors. The scout interceptor is timed to intercept an ICBM bus 2305 at the initial stages of RV deployment. The detector of the present invention is used to measure the direction and energy of the emitted gamma rays for each of the RVs in real time. The images of the RVs obtained by the onboard radar or infrared sensors can be superimposed onto the computer simulation provided by the present invention as illustrated in FIG. 24, thus allowing decoys 2307 to be rapidly distinguished from warheads 2309. In the scenario shown in FIG. 24, target RV 2401 is a decoy.

In the present application, the flight time prior to impact is quite short, resulting in negligible diffuse cosmic background gamma ray flux on the order of 0.6 photons in a 10 millisecond period. As scout interceptor 2303 approaches target 2401, the images of the RVs move radially outward from the center of the field-of-view. The direction of motion of the RVs can be determined in real time from the information obtained by the detection system of the present invention. This information as well as the information on which RVs contain warheads can either be transmitted to the ground control or to the interceptors following the scout.

Figure 25:
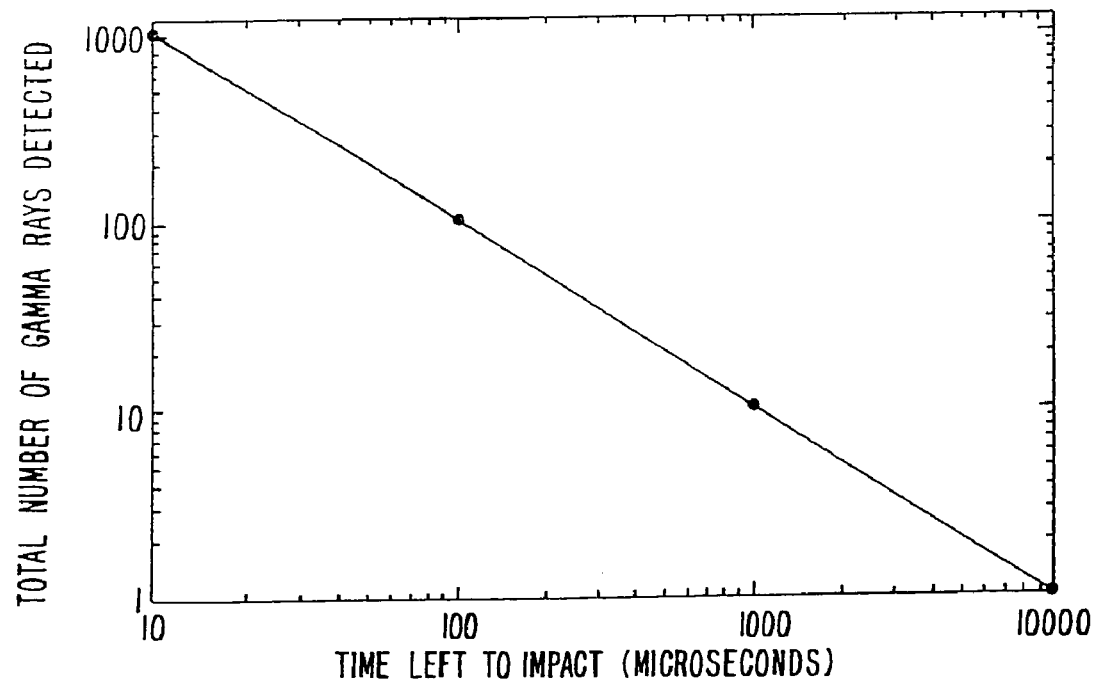
FIG. 25 is a graph of the number of integrated gamma ray photons versus time before impact for a nuclear warhead producing $5 \times 10^8$ gamma rays per second.
Figure 26:
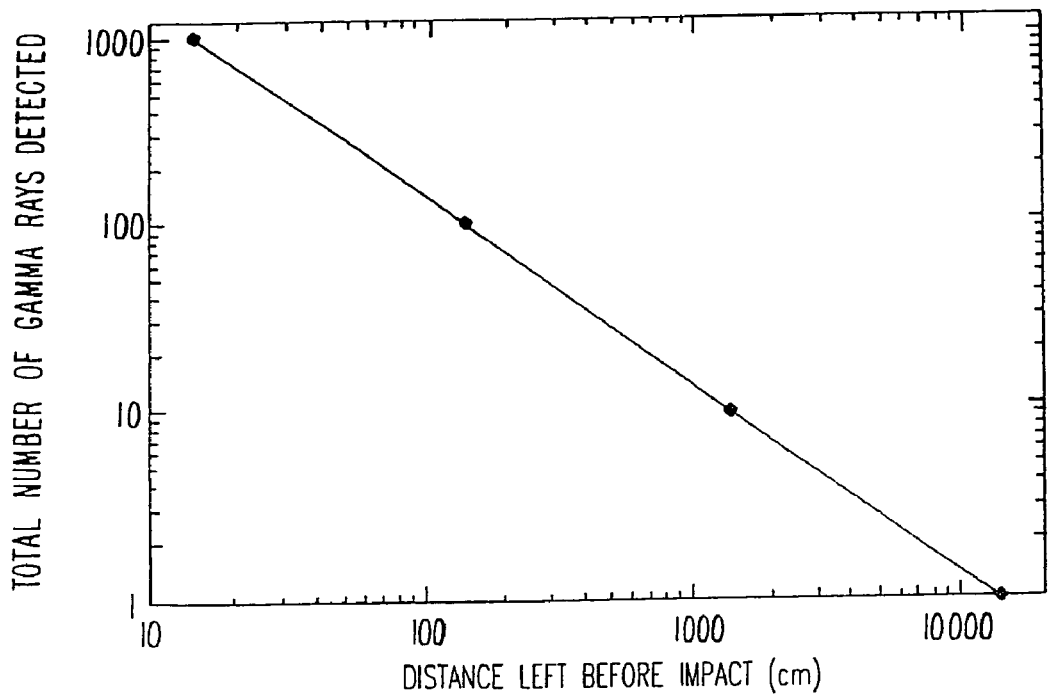
FIG. 26 is a graph of the number of integrated gamma ray photons versus distance before impact for a nuclear warhead producing $5 \times 10^8$ gamma rays per second.

FIGS. 25 and 26 show the results of the calculation of the total number of photons detected against time or distance before impact, assuming that the nuclear warhead encapsulated within the carrier missile produces $5 \times 10^8$ gamma rays per second. The area-efficiency factor for the present embodiment of the invention is taken as 500 square centimeters. The RVs and the scout missile are assumed to approach each other at a rate of 7 kilometers per second. The formula for the accumulated counts, C, is derived by integrating the count rate formula:

$$dC/dt = (LA\epsilon)/(4\pi R^2) = \{(LA\epsilon)/(4\pi [vt]^2)\}$$

to obtain the formula for counts:

$$C = \{(LA\epsilon)/(4\pi v^2)\}\{(1/t_1) - (1/t_0)\}$$

where L is the source luminosity ($5 \times 10^8$ γ/s), $A\epsilon$ is the area-efficiency factor (i.e., 500 cm$^2$), R is the distance to the source, v is the approach speed (14 km/s), $t_0$ and $t_1$ are the time to impact at the start and at the end of integration. If $t_0$ is large compared to $t_1$, C is proportional to $1/t_1$.

As the distance between the scout interceptor and the target decreases, the number of detected photons increases by a factor of $1/t_{to\ impact}$. The detection of a significant number of photons starts at approximately 10 milliseconds before impact. The 10 millisecond time before impact is equal to a distance of about 140 meters. In the 10 millisecond time interval, the number of diffuse galactic background gamma ray photons ($F_{Diff} = 1.1 \times 10^{-2} E^{-2.3}$ photons cm$^{-2}$s$^{-1}$sr$^{-1}$ MeV$^{-1}$) detected is negligible (i.e., approximately 0.6 photons). Since there is practically no background counts during the observation interval, even a few gamma rays detected from the source are significant especially if the detected gamma rays coincide with the position of one or more of the monitored RVs.

Therefore the proposed technique requires 10 milliseconds to detect, analyze, and transmit the information to the ground control or to the interceptors following the scout. The information to be transmitted contains the number of RVs, their position and direction of motion, and the identity of the RVs containing warheads. If additional discrimination time is required, either a slower scout interceptor missile can be used or the area-efficiency factor of the detection system can be increased.

The application of the invention illustrated in FIGS. 23 and 24 assume that the RVs are all deployed within a relatively short time. An alternative approach is for the RVs to be deployed one by one. In such a case a different technique can be applied in which the scout approaches the first RV in a collision course. If the scout determines that the first RV is a decoy, it alters its direction to bypass the first RV and initiates a collision course with the second RV. This process continues until a RV containing a warhead is detected. Once such a RV is detected, the interceptor is allowed to collide with the RV, destroying it in mid-course. One method of improving this technique is to use a slow scout interceptor with high maneuverability.

In an alternate configuration, the scout interceptor is aimed to meet and follow the ICBM bus or the RVs. This technique allows much longer observation times for the scout, on the order of minutes compared to milliseconds for the head-on interception. Assuming an observation time of approximately 5 minutes and a requirement of 20 counts per RV to detect the warheads with high significance and without ambiguity, then the maximum range of warhead detection is about 5.5 kilometers. In 5 minutes, the diffuse galactic gamma ray background radiation produces approximately 1 gamma ray event per 1° by 1° sky bin which is the FWHM angular resolution. Therefore, the minimum signal to noise ratio is about 20. This technique can be effective for exoatmospheric midcourse warhead discrimination if fast deployment of scout interceptors can be achieved.

Alternatively, the present invention can be used to observe covert satellites carrying nuclear warheads, assuming that the warheads have similar gamma ray emissions as the missile based warheads described above. In this case the present detection system could be tens of kilometers away, assuming a detection time on the order of hours in order to provide a statistically significant number of photons. Assuming a distance of 1 kilometer, an energy spectrum of 10,000 photons can be obtained within about one hour. The higher energy photons above 1 MeV with the characteristic nuclear lines can be used as the signal for final identification.

In another configuration the RVs can be irradiated, for example using a directed energy weapon, particle beam, or small scale neutron bomb, and the produced secondary emission can be used for discrimination purposes. In this configuration much higher numbers of gamma rays are expected, leading to warhead discrimination at distances on the order of 1,000 kilometers. The estimated gamma ray rate that may be observed from a neutral particle beam irradiated warhead at a range of 1,000 kilometers is 0.1 to 1 photon cm$^{-2}$s$^{-1}$. Therefore in 1 second 50 to 500 photons with energies reaching up to 10 MeV will be observed from such an interaction. This allows the detection system of the present invention to be mounted on a stationary space based platform. Its insensitivity to neutrons, wide field-of-view and imaging capability will enable discrimination and/or kill determination within a few seconds of the interaction.

An intact warhead contains significant amounts of shielding inside thus significantly reducing the amount of gamma rays observed from the outside as long as the casing is intact.

During a kill the warhead structure is disrupted, leading to a much larger release of gamma rays that can last for seconds. Assuming a factor of 1,000 increase in the gamma ray flux, a detection system according to the present invention as described above is expected to detect 100 gamma rays from the killed warhead for a duration of 1 second and at a distance of about 5 kilometers.

Precursor nuclear blasts can be employed in space before a nuclear attack in order to disrupt communications and defense systems. During such a blast the number of gamma rays released is extensive. For example, at 1,000 kilometers the gamma ray flux from a one megaton fission yield is approximately $10^7$ photons $cm^{-2}$ $s^{-1}$ with energies reaching up to 10 MeV. The present invention can be used to monitor such explosions from a distance and determine their position, extent, and duration. At the above photon fluxes, a small detection system in accordance with the present invention can be mounted on a fixed space platform to monitor precursor blasts from distances in excess of 10,000 kilometers. The same detection system could also be used to monitor nuclear powered satellites.

Inspection System

Figure 27:
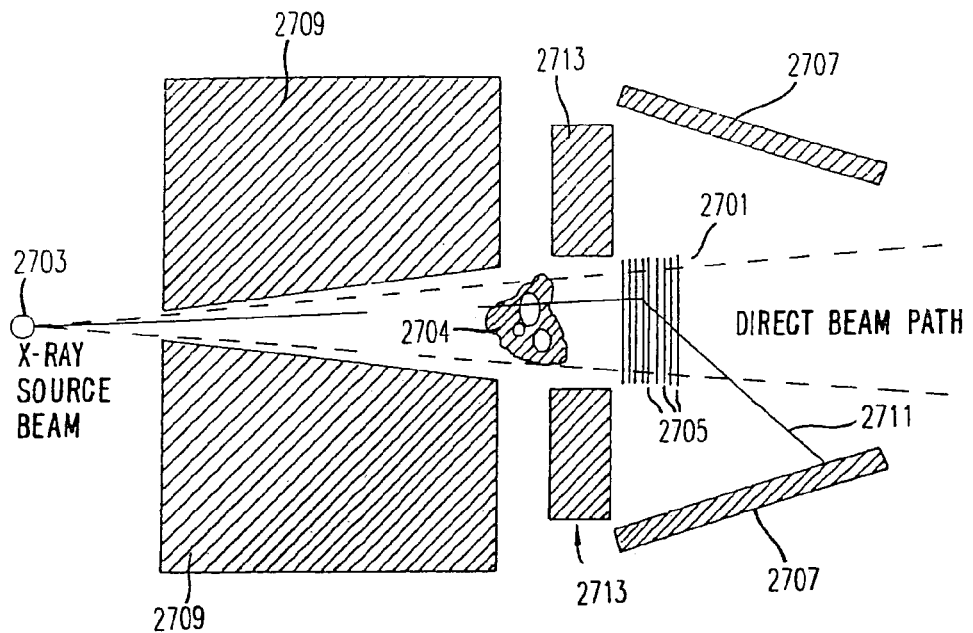
FIG. 27 is an illustration of an embodiment of the invention for use as a 2-dimensional inspection imaging system.

In another embodiment of the invention illustrated in FIG. 27, the detection system is used with 80 to 2,000 keV x-rays to provide a 2-dimensional imaging system, for example for use as a real-time munitions inspection system. FIG. 27 is an illustration of an embodiment of the invention for use as a 2-dimensional inspection imaging system.

A strong x-ray source is required for real-time inspection of munition items with 2-dimensional imaging. As this configuration requires that at least some portions of the detector be in the direct path of the x-ray beam, the system must be highly resistant to radiation damage. In the illustrated embodiment of the invention, only the active area of silicon microstrip hodoscope 2701 is in the direct path of the x-ray beam, a portion of the detection system which is expected to exhibit negligible effects under the desired x-ray source flux. The radiation damage to the FEE chips is also insignificant as these chips, in the preferred embodiment of the invention, are placed at the perimeter of the hodoscope and are therefore effectively shielded from the incident x-ray beam. Alternatively, the FEE chips may be manufactured using radiation hardened electronic circuits.

In one embodiment of the invention, a source 2703 provides x-rays of relatively low energy, on the order of 80 to 300 keV. In this embodiment the detection system only uses silicon microstrip hodoscope 2701 as opposed to a combination of a hodoscope and a calorimeter. For imaging a small object 2704, the area of each detection plane 2705 of hodoscope 2701 is typically between approximately 16 square centimeters and 144 square centimeters with a plane thickness of between 0.5 and 1 millimeter. Assuming a total silicon thickness of between about 2 and 10 centimeters, the Compton scatter probability ranges from 45 to 95 percent for 300 keV x-rays. Pixel sizes can be as low as approximately 625 square micrometers for super high resolution imaging. The object size must be at most equal to the detector area, otherwise only a section of the object is imaged.

The detector of this embodiment can be used with both energy and angular discrimination of the scattered photon background. In the single scatter mode it will accumulate all events without any cut. In the double scatter mode it will measure the total energy deposited in the hodoscope from multiple Compton scatters ending most likely with photo-absorption. The direction of the incident photon can also be determined from the energies deposited at each interaction point and the pixel coordinates of the first and the last scatters. As this embodiment does not include a calorimeter section, it exhibits excellent energy and angular resolution and can be used with both monoenergetic and continuous energy x-ray sources.

Although the present hodoscope only embodiment can be used with a higher energy x-ray source 2703 in order to accommodate larger objects 2704, this approach would require that detection planes 2705 have a much larger area and that hodoscope 2701 be comprised of many more planes 2705. A more practical solution is to combine hodoscope 2701 with a calorimeter 2707 placed behind a collimating shield 2709.

As illustrated in FIG. 27, the collimated x-ray beam from source 2703 is incident on object 2704 under inspection. Although collimating shield 2709 may not be necessary if the x-ray beam is already collimated to the size of hodoscope 2701, preferably shield 2709 is used to shield calorimeter 2707 and the hodoscope electronics from the x-ray source.

Calorimeter 2707 surrounds the sides of silicon microstrip hodoscope 2701. As illustrated, an x-ray photon 2711 that is unscattered in object 2704 makes a Compton scatter in one of the silicon microstrip hodoscope planes 2705 and stops in calorimeter 2707. Whether or not a detected photon from a monoenergetic source is scattered in the test object will be determined by the total energy of the photon deposited in the detector. The elimination of the photons scattered in the test object significantly decreases the background and enhances the signal-to-noise ratio. Calorimeter 2707 can also be shielded from the background photons scattered in the test object by placing a separate shield 2713 between test object 2704 and calorimeter 2707, thereby reducing the calorimeter count rates.

In this embodiment, source 2703 is monoenergetic in the range of about 300 to 2,000 keV. Suitable sources include $Cs^{137}$ and $Co^{60}$. Energy cuts within the detector energy resolution are sufficient to eliminate much of the scattered photon background.

The preferred embodiment of the munitions inspection system can be used with both monoenergetic and continuous energy sources (e.g., 80 to 2,000 keV) for medium to large size test objects. In this embodiment the calorimeter must be position sensitive to enable the determination of the incident photon direction. To achieve sufficiently good direction determination the hodoscope pixel size is preferably less than 1 square millimeter and the calorimeter pixel size is preferably less than 1 square centimeter. The calorimeter preferably absorbs Compton scattered photons with about 90 percent efficiency.

Figure 28:
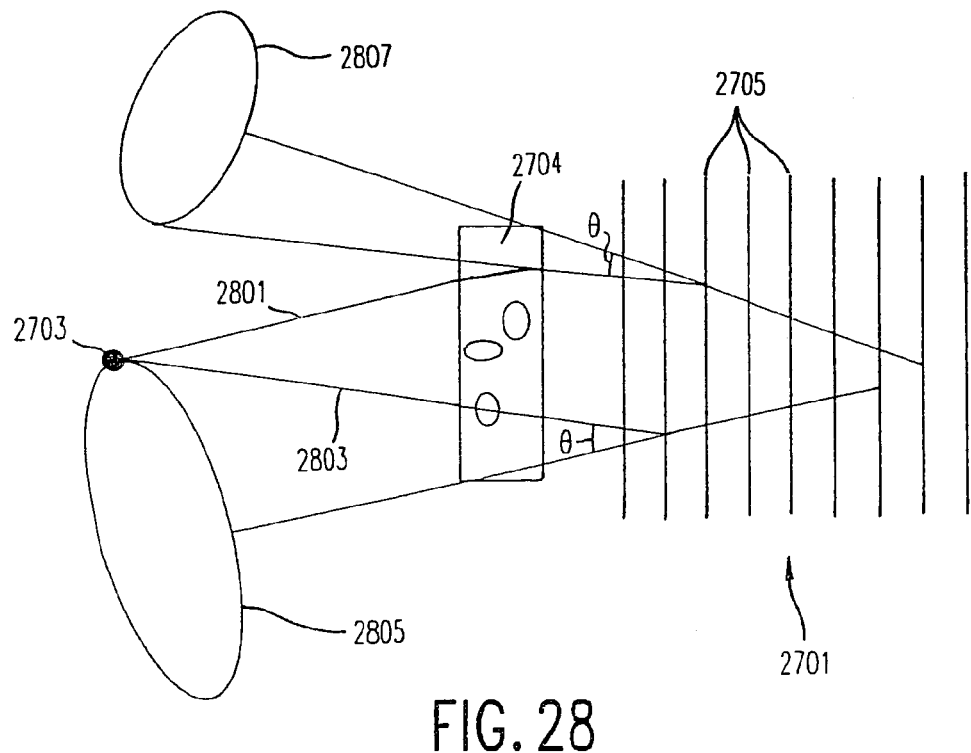
FIG. 28 is an illustration of the scattered photon background discrimination technique using the incident photon direction measurement.

In this embodiment the scattered photon background is eliminated by measuring the incident photon direction. FIG. 28 demonstrates the method of discrimination of the scattered photon background. The figure shows an x-ray 2801 scattered in test object 2704 as well as an unscattered x-ray 2803. The Compton scatter angle is calculated using the formula given above from the energies deposited in the two interaction points, assuming that the photon is totally absorbed in the second scatter. The scattered photon vector is determined from the coordinates of the first two interaction point pixels in the hodoscope. An event ring 2805 determined for the unscattered event passes through the known x-ray source direction while an event ring 2807 for the scattered event does not.

Depending on the energy resolution and the geometry of the two pixels, some of the event rings from scattered photon background may overlap the point source direction. Higher energy and geometric resolution improves scattered photon background. A much more significant improvement can be made if the first recoil electron is tracked through the hodoscope. This will limit the event ring to an arc and the chance probability of a scattered photon arc with the x-ray source direction diminishes dramatically.

Another embodiment of the invention is an energy resolved tomography imager for use with a continuous x-ray source. In addition to background discrimination using the incident photon direction measurement for a continuous energy x-ray source, the energies of the unscattered photons are determined. The energy spectrum for each image pixel can be measured leading to an energy resolved tomography imaging system, assuming that either the test object or the detector is rotated. This system can also produce two-dimensional images with energy spectrum information.

The Compton scatter depends strongly on the electron content of the material the x-ray beam traverses. Therefore the energy spectrum obtained for each pixel represents, with inverse proportionality, the electron content in the test object along that path. The different energy spectra can be represented by different colors and the intensity can be represented as the brightness of individual colors. This system can be used for real-time imaging of objects (e.g., munitions), medical imaging, and radiography.

In this embodiment calorimeter 2707 is position sensitive and is comprised of CsI(Tl) crystals. The crystals are preferably rectangular bars with cross-sectional areas in the range of 1 square centimeter to 6.25 square centimeters with a length in the range of approximately 1.5 to 2.5 centimeters. The length is primarily driven by the detection energy range. The bottom portion of the calorimeter requires longer crystals since the forward scattered gamma rays carry most of the primary photon energy, thus providing extra thickness to stop the higher energy. The CsI(Tl) crystals on the top portion of the calorimeter can be short, as the photons with large Compton scatter angles carry a smaller fraction of the primary photon energy. Therefore in this embodiment the calorimeter is comprised of a mosaic of individual CsI(Tl) crystals. Since each crystal is individually viewed by a photodiode, the system requires the same number of photodiodes as crystals.

Assuming a data rate of 100 kHz to 1 MHz, 1 millimeter thick hodoscope silicon detector planes with a 25 square centimeter area, and a factor of 100 photon attenuation at the test object, a 662 keV energy x-ray source with a maximum of $2 \times 10^9$ photons per square centimeter per second (unattenuated at the hodoscope) can be utilized in the present embodiment. At a 1 MHz data acquisition rate, approximately 10,000 events are accumulated in 1 second per 1 square millimeter pixel, assuming 25 hodoscope planes while at 10 MHz approximately 100,000 events are accumulated per pixel. Therefore sufficient information is obtained in seconds for real-time imaging.

Figure 29A:
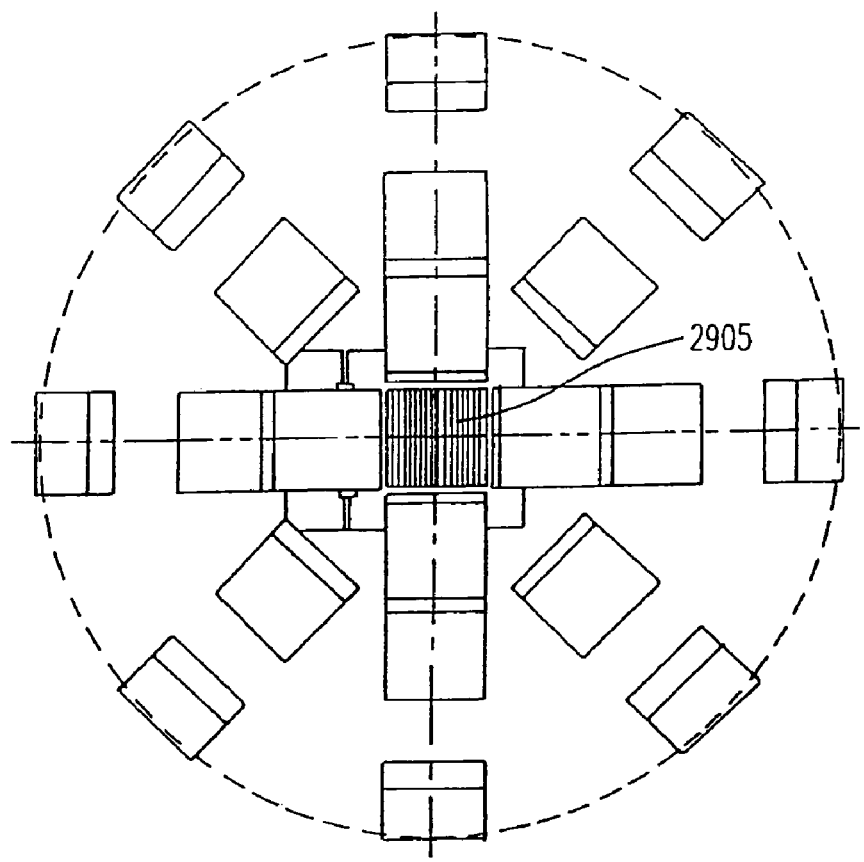
FIGS. 29A and B are an illustration of a configuration of the invention in which a plurality of CsI(Tl)/photodiode modules are placed on a hemisphere with most detection modules placed in a forward direction with respect to the incident beam.
Figure 29B:
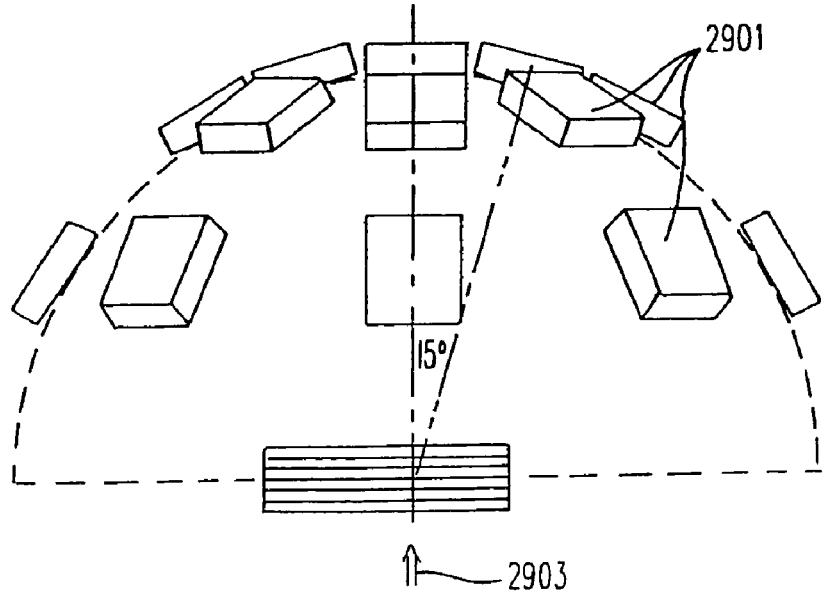

In one embodiment, the calorimeter modules are positioned close to the forward direction in order to obtain higher angular resolution and detector efficiency. FIG. 29 is an illustration of a configuration in which a plurality CsI(Tl)/photodiode modules 2901 are placed on a hemisphere, preferably with a radius of approximately 50 centimeters. More detector modules 2901 are placed in the forward direction with respect to incident beam 2903. A hole 2905 with a 15° solid angle is left at the center of the calorimeter to allow unscattered photons to pass.

Positron Imaging System

The positron is the antiparticle of the electron which has the same mass but opposite charge. Some radionuclides reduce their excessive positive nuclear charge by the emission of positrons. After a positron is emitted from a radionuclide it loses its kinetic energy through a series of ionizations and excitations in matter until it slows down and forms an atom-like structure called "positronium" with an electron. Positronium has a very short life time, $10^{-10}$ seconds for the para state, and annihilates into a pair of photons in the para state or into 3 photons in the ortho state. Approximately 99.7 percent of the annihilation radiation comes from the para state since the ortho state has to go through a forbidden transition. Since both the electron and the positron are nearly at rest, to conserve energy and momentum the two photons fly off in opposite directions in an early perfect straight line, each carrying an energy of about 511 keV which is the rest mass of electron and positron. There is a slight non-collinearity of about $180° \pm 0.25°$ due to the small but finite energy of the positronium just before annihilation.

The present invention can be used to observe the presence of positrons in tissues by detecting the generated annihilation radiation. The simultaneous emission of two photons traveling in opposite directions renders this process extremely effective.

The table below shows some of the positron sources that can be used as radio-tracers with the present invention. Since most of these sources are radioactive counterparts of normal constitutes of living beings, they are excellent for the production of radiopharmaceuticals. Their short life-times are also useful in administration of large doses without the risk of significant radiation exposure to the patient. Fluorine-18 is the preferred radio-tracer since it has the shortest range in body tissue (i.e., approximately 2.4 millimeters) and the longest life-time (i.e., approximately 109.7 minutes).

| Radionuclide | Half-Life (min) | End-Point Energy (MeV) | % β+ Decay | Max Range (mm) |
|---|---|---|---|---|
| Carbon-11 | 20.4 | 0.97 | 99.8 | 4.1 |
| Nitrogen-13 | 9.96 | 1.19 | 100.0 | 5.1 |
| Oxygen-15 | 2.07 | 1.7 | 99.9 | 7.3 |
| Fluorine-18 | 109.7 | 0.635 | 96.9 | 2.4 |
| Gallium-68 | 68.1 | 1.88 | 90.0 | 8.1 |
| Bromine-75 | 101.0 | 1.70 | 76.0 | 7.3 |
| Strontium-82 | 1.3 | 3.15 | 96.0 | 15.6 |

Figure 30:
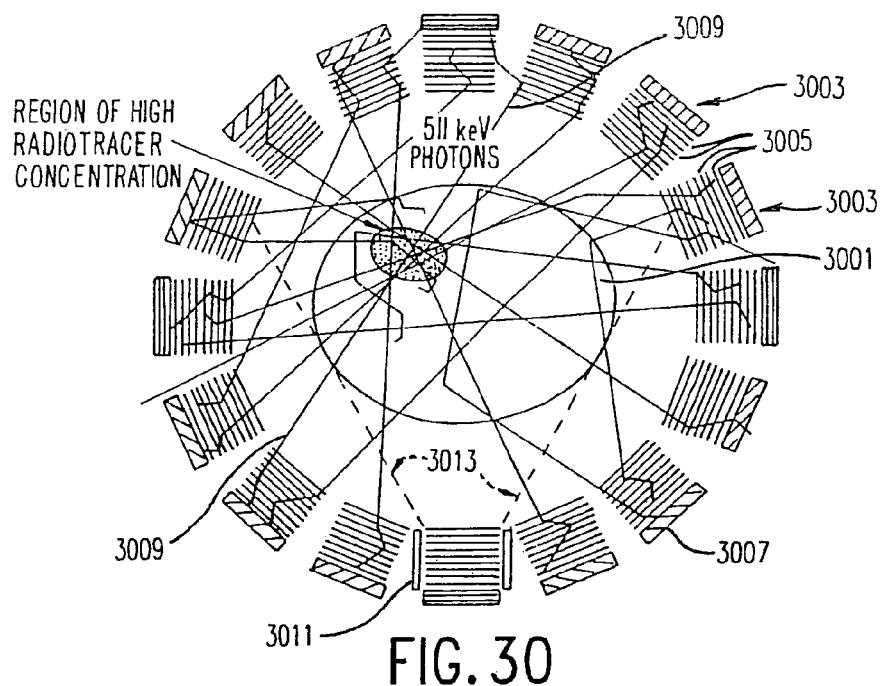
FIG. 30 is an illustration of an embodiment of a positron imaging system according to the present invention.

An embodiment of positron imaging system according to the present invention is shown in FIG. 30. As illustrated, an object 3001 such as a human skull is surrounded by a plurality of detection systems 3003. Each detection system 3003 is comprised of strip detectors 3005 and a calorimeter 3007. Preferably the systems use CdZnTe strip detectors and CdZnTe calorimeters.

The first interaction point in CdZnTe strip detectors 3005 gives the coordinates of the Compton interaction within a 4 square millimeter pixel size, assuming that double-sided strip detectors are used in orthogonal strips on each side and a pitch of 2 millimeters. The coincident detection in two different detector banks defines a positron annihilation photon pair chord, such as pair 3009. By positioning strip detector planes 3005 extremely close to one another, the detector depth can be reduced. The size of the detector planes can be increased progressively in the radial direction to reduce the gap between each detector bank or the CdZnTe strip detectors can be placed overlapping each other by increasing the plane separation.

As illustrated, photon pairs are created inside the tissue of object 3001 from positron annihilations and detected in CdZnTe strip detectors 3005 by undergoing Compton scattering and photoelectric absorption. Photons can also be scattered inside the tissue, thereby producing the scattered photon background. Other photons are absorbed in the body and produce the gamma ray attenuation that can be corrected by well known methods. These background photons have lower energies because of initial scatterings and are rejected as described above. Occasionally photons will make more than one Compton scatter in a CdZnTe strip detector bank. These are legitimate events as the full energy of the photon is measured by adding the energies observed at each interaction point. Some photons may escape with significant energy after the last interaction. These events will be rejected as scattered photon background. The stopping power of the whole detector can be matched to that of BGO crystals by either increasing the number of CdZnTe strip detectors or putting a calorimeter plane at the back of the CdZnTe strip detectors as illustrated in FIG. 30. The present invention can also be made in an elliptical or curved shape to fit the contours of the human body since the 8 cubic millimeter voxel size virtually eliminates the radial elongation. The detector can be protected from photons coming from different parts of the patient by using a shield 3011 (e.g., lead) around the outer perimeter of each detection system 3003.

The coincidence setup follows the fan angle technique. Fan tangents 3013 are drawn from each detector bank to the organ under study as shown in FIG. 30. The banks which are covered by the fan beam are put in coincidence with the originator. A smaller number of banks (e.g., 16) make this complex technique feasible.

Figure 31:
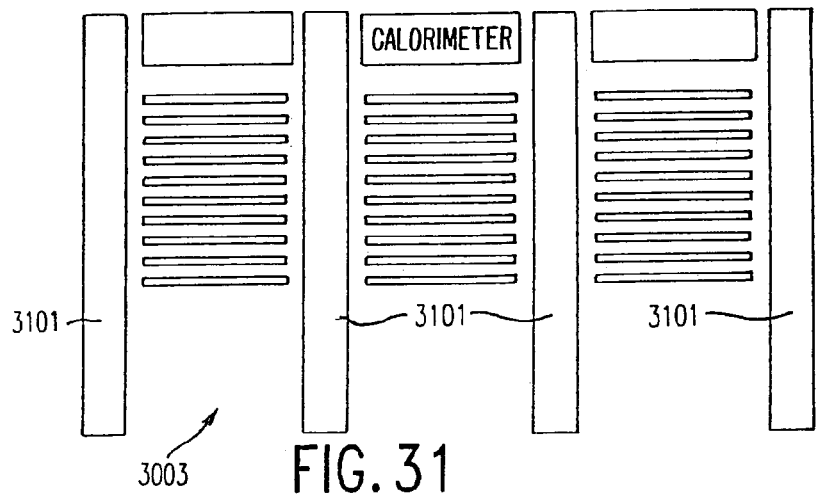
FIG. 31 is an illustration of the cross-section of a portion of a positron imager detection system in which the individual hodoscopes are separated by calorimeter septa.

In an alternate embodiment illustrated in part in FIG. 31, each detection system 3003 is separated by a calorimeter septa 3101. If individual hodoscope/calorimeter modules are used as shown in FIG. 30, the modules can either completely surround the patient or some even number of diametrically opposed modules can be used. In the latter case, the detector modules may be rotated to form the desired tomographic images.

Figure 32:
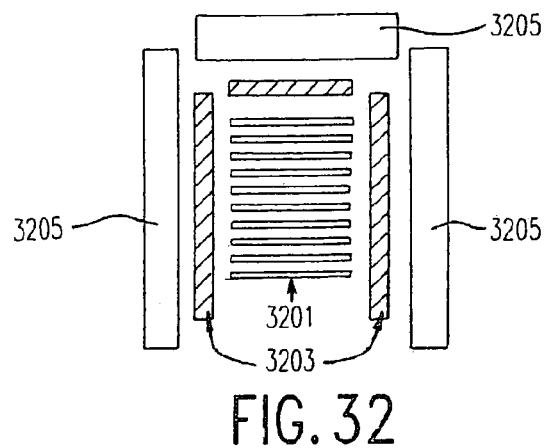
FIG. 32 is an illustration of the cross-section of a detector module with inner and outer calorimeter sections.

In another embodiment of the detection modules illustrated in FIG. 32, the calorimeter is built from two sections. Surrounding hodoscope 3201 is a thin inner detector 3203. Surrounding detector 3203 is a thick outer detector 3205. Inside detector 3203 can be made from CdZnTe strip or pad detectors to produce fine position resolution. Outer detectors 3205 can be thicker and may have fine or even low spatial resolution. The calorimeter and hodoscope are shown in rectangular structure but in actual implementation they can have any shape, for example they can be curved into spherical or parabolic configurations to maximize the efficiency, sensitivity, angular and energy resolutions.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A detector system for detecting at least one particle, said detector system comprising:
    at least one position sensitive detector wherein said at least one particle produces a plurality of electron-hole pairs inside at least one of said at least one position sensitive detector;
    at least one carrier with a first side coupled to said at least one position sensitive detector, wherein said at least one carrier comprises at least one conductive path; and
    at least one integrated circuit with at least one input coupled to a second side of said at least one carrier,
    wherein at least one of a plurality of electrons and a plurality of holes from said plurality of electron-hole pairs travels from said at least one position sensitive detector through said at least one conductive path to at least one of said at least one input, and
    wherein said at least one integrated circuit processes at least one of said plurality of electrons and said plurality of holes to produce at least one output.

2. The detector system of claim 1, wherein said at least one position sensitive detector is selected from the group consisting of a pixel detectors, strip detectors, double sided pixel detectors and double sided strip detectors.

3. The detector system of claim 1, wherein the detector material of said at least one position sensitive detector is selected from the group consisting of HpGe, Ge, CdTe, CdZnTe, $HgI_2$, GaAs, $PbI_2$, CsI(Tl), $CdWo_4$, CsF, NaI(Tl), CsI(Na), BGO, LSO, $PbCO_3$ and GSO.

4. The detector system of claim 1, wherein said at least one position sensitive detector is at least two position sensitive detectors.

5. The detector system of claim 1, wherein at least one of said at least one position sensitive detector is a direct conversion detector.

6. The detector system of claim 1, wherein said at least one particle is selected from the group consisting of photons, electrons, positrons, protons, alpha particles, x-rays and gamma rays.

7. The detector system of claim 6, wherein at least one of said photons, said x-rays and said gamma-rays make at least one Compton scatter inside at least one of said at least one position sensitive detector.

8. The detector system of claim 6, wherein at least one of said photons, said x-rays and said gamma-rays interacts through photoelectric effect and is absorbed inside at least one of said at least one position sensitive detector.

9. The detector system of claim 6, wherein at least one of said photons and one of said gamma-rays interacts through pair production and creates an electron-positron pair inside at least one of said at least one position sensitive detector.

10. The detector system of claim 1, wherein said detector system is four-sides abuttable.

11. The detector system of claim 1, wherein said at least one output is at least one image.

12. The detector system of claim 1, wherein said at least one carrier includes peripheral electronics.

13. A detector system for detecting a plurality of particles, said detector system comprising:
    a plurality of position sensitive detectors, wherein a portion of said plurality of particles produces a plurality of electron-hole pairs inside at least one of said plurality of position sensitive detectors;
    a plurality of carriers, wherein a first side of at least one portion of said plurality of carriers is coupled to at least one portion of said plurality of position sensitive detectors, wherein at least one portion of said plurality of carriers comprises a plurality of conductive paths; and
    a plurality of integrated circuits with a plurality of inputs coupled to a second side of at least one portion of said plurality of carriers,
    wherein at least one of a plurality of electrons and a plurality of holes from said plurality of electron-hole pairs travels from at least one portion of said plurality of position sensitive detectors through at least one portion of said plurality of conductive paths to at least one portion of said plurality of inputs, and wherein at least one of said plurality of integrated circuits process at least one of said plurality of electrons and said plurality of holes to produce at least one output.

14. The detector system of claim 13, wherein said plurality of position sensitive detectors are selected from the group consisting of pixel detectors, strip detectors, double sided pixel detectors and double sided strip detectors.

15. The detector system of claim 13, wherein the detector material of said plurality of position sensitive detectors is selected from the group consisting of HpGe, Ge, CdTe, CdZnTe, $HgI_2$, GaAs, $PbI_2$, CsI(Tl), $CdWo_4$, CsF, NaI(Tl), CsI(Na), BGO, LSO, $PbCO_3$ and GSO.

16. The detector system of claim 13, wherein at least one portion of said plurality of particles are selected from the group consisting of photons, electrons, positrons, protons, alpha particles, x-rays and gamma rays.

17. The detector system of claim 16, wherein at least one of said photons, said x-rays and said gamma-rays make at least one Compton scatter inside at least one of said plurality of position sensitive detectors.

18. The detector system of claim 13, wherein said at least one position sensitive detector is selected from the group consisting of strip detectors, pixel detectors, double sided pixel detectors and double sided strip detectors.

19. A detector system for detecting at least one particle, said detector system comprising:
at least one pixel detector, wherein said at least one particle produces a plurality of electron-hole pairs inside at least one of said at least one pixel detector;
at least one carrier with a first side coupled to said at least one pixel detector, wherein said at least one carrier comprises at least one conductive path; and
at least one integrated circuit with at least one input coupled to a second side of said at least one carrier,
wherein at least one of a plurality of electrons and a plurality of holes from said plurality of electron-hole pairs travels from said at least one pixel detector through said at least one conductive path to at least one of said at least one input, and
wherein said at least one integrated circuit processes at least one of said plurality of electrons and said plurality of holes to produce at least one output.

20. The detector system of claim 19, wherein at least one of said at least one pixel detector is selected from the group consisting of one-side, two-side, three-side and four-side abuttable design.

21. The detector system of claim 19, wherein said at least one particle is selected from the group consisting of photons, electrons, positrons, protons, alpha particles, x-rays and gamma rays.

22. The detector system of claim 21, wherein at least one of said photons, said x-rays and said gamma-rays make at least one Compton scatter inside at least one of said at least one pixel detector.

23. A method for producing a four side abuttable detector module for detecting a plurality of particles, said method comprising:
mounting at least one position sensitive detector onto a first side of at least one carrier having same or smaller size and containing a plurality of conductive paths;
coupling at least one integrated circuit to a second side of said at least one carrier;
limiting at least one of said at least one carrier dimensions not to exceed at least one of said at least one position sensitive detector dimensions;
detecting a portion of said plurality of particles by at least one of said at least one position sensitive detector and producing a plurality of signals;
connecting at least one portion of said plurality of signals to at least one portion of said plurality of inputs using at least one portion of said plurality of conductive paths; and
processing said plurality of signals by said at least one integrated circuit and producing at least one output.

24. The method detector of claim 23, wherein at least one of said at least one position sensitive detector is selected from the group consisting of pixel detectors, strip detectors, double sided pixel detectors and double sided strip detectors.

25. The method of claim 23, wherein at least one portion of said plurality of particles are selected from the group consisting of photons, electrons, positrons, protons, alpha particles, x-rays and gamma rays.

26. The detector system of claim 23, wherein at least one portion of said plurality of particles are selected from the group consisting of photons, electrons, positrons, protons, alpha particles, x-rays and gamma-rays.

27. The detector system of claim 26, wherein at least one of said photons, said x-rays and said gamma-rays make at least one Compton scatter inside at least one of said plurality of strip detectors.

28. A detector system for detecting a plurality of particles, said detector system comprising:
at least one detector wherein each one of said at least one detector comprises at least one scintillator coupled to at least one solid-state light detector;
wherein a portion of said plurality of particles produces a plurality of scintillation light inside said at least one scintillator; wherein at least one portion of said a plurality of scintillation light produces a plurality of electron hole pairs inside at least one of said at least one solid-state light detector;
wherein said at least one detector is mounted on at least one side of at least one board, wherein said at least one board comprises at least one conductive path;
wherein at least one integrated circuit with a plurality of inputs is mounted on at least one side of said at least one board;
wherein at least one of a plurality of electrons and a plurality of holes from said plurality of electron-hole pairs travel from said at least one solid-state light detector detector through said at least one conductive path to at least one portion of said plurality of inputs; and
wherein said plurality of integrated circuits process at least one of said plurality of electrons and said plurality of holes to produce at least one output.

29. The detector system of claim 28, wherein said scintillator material is selected from the group consisting of CsI(Tl), $CdWo_4$, CsF, NaI(Tl), CsI(Na), BGO, LSO, $PbCO_3$ and GSO.

30. The detector system of claim 28, wherein said solid-state light detector is selected from the group consisting of diodes, photodiodes, PIN photodiodes, and avalanche photodiodes (APDs).

31. The detector system of claim 28, wherein at least one portion of said plurality of particles are selected from the group consisting of photons, electrons, positrons, protons, alpha particles, x-rays and gamma rays.

32. The detector system of claim 31, wherein at least one of said photons, said x-rays and said gamma-rays make at least one Compton scatter inside at least one of said at least one scintillator.

33. A detector system for imaging a plurality of particles, said detector system comprising:

a plurality of pixel detectors, wherein portion of said plurality of particles produces a plurality of electron-hole pairs inside at least one of said plurality of pixel detectors;

a plurality of carriers, wherein a first side of at least one portion of said plurality of carriers is coupled to at least one portion of said plurality of pixel detectors, wherein at least one portion of said plurality of carriers comprises at least one conductive path; and a plurality of integrated circuits with a plurality of inputs coupled to a second side of at least one portion of said plurality of carriers;

at least one of a plurality of electrons or a plurality of holes from said plurality of electron-hole pairs travels from said at least one portion of said plurality of pixel detectors through at least one of said at least one conductive path to at least one portion of said plurality of inputs, and wherein at least one of said plurality of integrated circuits process at least one of said plurality of electrons and said plurality of holes to produce at least one image.

34. The detector system of claim 33, wherein at least one portion of said plurality particles are selected from the group consisting of photons, electrons, positrons, protons, alpha particles, x-rays and gamma rays.

35. The detector system of claim 34, wherein at least one of said photons, said x-rays and said gamma-rays make at least one Compton scatter inside at least one of said plurality of pixel detectors.

36. At least one detector module for detecting a plurality of particles, said at least one detector module comprising:

at least one position sensitive detector which produces a plurality of signals from at least a portion of said plurality of particles;

at least one carrier with a plurality of conductive paths;

at least one integrated circuit with a plurality of inputs;

wherein at least one of said at least one position sensitive detector is coupled to a first side of at least one of said at least one carrier;

wherein at least one of said at least one integrated circuit is coupled to a second side of at least one of said at least one carrier;

wherein said plurality of conductive paths connects at least one portion of said plurality of signals to at least one portion of said plurality of inputs;

wherein at least one of said at least one integrated circuit processes at least one portion of said plurality of signals and produces at least one output; and wherein said at least one detector module is configured to abut at least one other of said at least one detector module on any one of four sides of at least one of said at least one detector module.

37. The detector module of claim 36, wherein said plurality of particles are selected from the group consisting of photons, electrons, positrons, protons, alpha particles, x-rays and gamma rays.

38. At least one detector module for detecting a plurality of particles, said at least one detector module comprising:

at least one pixel detector with a plurality of pixels producing at least one signal from a portion of said plurality of particles;

at least one carrier with a plurality of connections;

at least one integrated circuit with a plurality of inputs;

wherein said at least one pixel detector mounted onto one side of said at least one carrier;

wherein said at least one integrated circuit mounted onto another side of said at least one carrier;

wherein at least one of said at least one carrier connects at least one of said at least one signal from at least one of said at least one pixel detector to at least one portion of said plurality of inputs using at least one portion of said plurality of connections;

wherein at least one of said at least one integrated circuit processes at least one of said at least one signal and produces at least one output; and wherein at least one of said at least one detector module is configured to abut at least one other of said at least one detector module on any one of four sides of at least one of said at least one detector module.

39. The detector module of claim 38, wherein said plurality of particles are selected from the group consisting of photons, electrons, positrons, protons, alpha particles, x-rays and gamma rays.

40. The detector system of claim 38, wherein said at least one detector module is abutted to at least one other detector module to produce a large detector array.

41. A method for detecting a plurality of particles using at least one detector module, said method comprising:

detecting a portion of said plurality of particles by at least one position sensitive detector and producing a plurality of signals;

coupling said at least one position sensitive detector onto a first side of at least one carrier containing a plurality of conductive paths;

coupling at least one integrated circuit with a plurality of inputs to a second side of said at least one carrier;

making said first side and said second side of said at least one carrier have an output area at most the size of said at least one position sensitive detector;

connecting said plurality of signals to said plurality of inputs using said plurality of conductive paths; and processing said plurality of signals by said at least one integrated circuit and producing at least one output.

42. The method for detecting a plurality of particles of claim 41, wherein at least one portion of said plurality of particles are selected from the group consisting of photons, electrons, positrons, protons, alpha particles, x-rays and gamma rays.

43. A method for detecting a plurality of particles using at least one detector module, said method comprising:

detecting a portion of said plurality of particles by at least one pixel detector and producing a plurality of signals;

mounting said at least one pixel detector onto a first side of at least one carrier containing a plurality of connections;

mounting at least one integrated circuit with a plurality of inputs to a second side of said at least one carrier;

making said first side and said second side of said at least one carrier to have an area equal or smaller than the size of said at least one position sensitive detector;

connecting said plurality of signals to said plurality of inputs using said plurality of connections; and processing said plurality of signals by said at least one integrated circuit and producing at least one output.

44. The method for detecting a plurality of particles of claim 43, wherein at least one portion of said plurality particles are selected from the group consisting of photons, electrons, positrons, protons, alpha particles, x-rays and gamma rays.

45. At least one four side abuttable detector module for detecting a plurality of particles, said detector module comprising:

at least one position sensitive detector mounted onto a first side of at least one carrier having same or smaller size and containing a plurality of conductive paths;

at least one integrated circuit with a plurality of inputs coupled to a second side of said at least one carrier, wherein the dimensions of at least one of said at least one carrier is limited not to exceed at least one of said at least one position sensitive detector dimensions;

wherein at least a portion of said plurality of particles produce a plurality of signals in at least one of said at least one position sensitive detector;

wherein at least one portion of said plurality of conductive paths connects at least one portion of said plurality of signals to at least one portion of said plurality of inputs; and wherein at least one of said at least one integrated circuit processes at least one portion of said plurality of signals and produces at least one output.

46. The method for detecting a plurality of particles of claim 45, wherein at least one portion of said plurality particles are selected from the group consisting of photons, electrons, positrons, protons, alpha particles, x-rays and gamma rays.

47. The detector system of claim 45, wherein said at least one four side abuttable detector module is abutted with at least one other detector module to produce a large detector array.

48. A method for detecting a plurality of particles using at least one detector module, said method comprising:

detecting a portion of said plurality of particles by at least one position sensitive detector and producing a plurality of signals, wherein said at least one position sensitive detector comprises at least one scintillator coupled to at least one solid-state light detector;

coupling said at least one position sensitive detector onto a first side of at least one carrier containing a plurality of connections;

coupling at least one integrated circuit with a plurality of inputs to a second side of said at least one carrier;

making said first side and said second side of said at least one carrier to have an area equal or smaller than the size of said at least one position sensitive detector;

connecting said plurality of signals to said plurality of inputs using said plurality of connections; and processing said plurality of signals by said at least one integrated circuit and producing at least one output.

49. The method for detecting a plurality of particles of claim 48, wherein said plurality of particles are selected from the group consisting of photons, electrons, positrons, protons, alpha particles, x-rays and gamma rays.

* * * * *